US006858576B1

(12) United States Patent
Young et al.

(10) Patent No.: US 6,858,576 B1
(45) Date of Patent: Feb. 22, 2005

(54) METHODS FOR REGULATING GASTROINTESTINAL MOTILITY

(75) Inventors: Andrew A. Young, San Diego, CA (US); Bronislava Gedulin, San Diego, CA (US); Nigel Robert Arnold Beeley, Solana Beach, CA (US); Kathryn S. Prickett, San Diego, CA (US)

(73) Assignee: Amylin Pharmaceuticals, Inc., San Diego, CA (US)

(*) Notice: Subject to any disclaimer, the term of this patent is extended or adjusted under 35 U.S.C. 154(b) by 310 days.

(21) Appl. No.: 08/908,867

(22) Filed: Aug. 8, 1997

Related U.S. Application Data

(63) Continuation-in-part of application No. 08/694,954, filed on Aug. 8, 1996, now abandoned.

(51) Int. Cl.[7] ........................ A61K 38/00; A61K 38/16; A61K 38/17; A61K 38/26; C07K 5/00

(52) U.S. Cl. .............................. 514/2; 514/12; 514/21; 530/300; 530/308

(58) Field of Search ................................ 514/2, 12, 21, 514/3; 530/300, 308; 424/9.1, 9.3

(56) References Cited

U.S. PATENT DOCUMENTS

| | | | | |
|---|---|---|---|---|
| 3,862,301 A | * | 1/1975 | Chernish et al. | 424/4 |
| 5,187,154 A | * | 2/1993 | Phillips et al. | 514/12 |
| 5,264,372 A | | 11/1993 | Beaumont et al. | |
| 5,424,286 A | * | 6/1995 | Eng | 514/2 |

FOREIGN PATENT DOCUMENTS

| | | | |
|---|---|---|---|
| WO | WO 95/07098 | * | 3/1995 |
| WO | WO 96/06628 | * | 3/1996 |
| WO | WO 98/05351 | | 2/1998 |
| WO | WO 98/30231 | | 7/1998 |
| WO | WO 99/07404 | | 2/1999 |

OTHER PUBLICATIONS

Dupre, J. et al. Glucagon–like peptide I reduces postprandial glycemic excursions in IDDM. Diabetes, 44: 626–630, Jun. 1995.*

Rai, A. et al. Actions of Helodermatidae venom peptides and mammalian glucagon–like peptides on gastric chief cells. Am. J. Physiol., 265 (gastrointest. Liver Physiol. 28): G118–G125, 1993.*

Daniel, O. et al. Use of glucagon in the treatment of acute diverticulitis. British Medical Journal, 3: 720–722, 1974.*

Vandermeeers et al, European Journal of Biochemistry, 1987, vol. 164, pp. 321–327.*

Strandberg et al (Acta Radiologica, 1988, vol. 29, pp. 49–52).*

GenBank Accession No. CAA24759, Feb. 9, 1999.*

Bayer et al., "Advances in Poison Management," *Clin. Chem.,* 42(8)(B):1361–66 (1996).

D'Alessio et al., "Glucagon–like Peptide 1 Enhances Glucose Tolerance Both by Stimulation of Insulin Release and by Increasing Insulin–independent Glucose Disposal," *J. Clin. Invest.,* 93:2263–66 (1994).

Holst, "Glucagonlike Peptide–1: A Newly Discovered Gastrointestinal Hormone," *Gastroenterology*, 107:1848–55 (1994).

Lawler et al., "Comparison of Effects of Amylin, Glucagon–like Peptide–1 (GLP–1) and Exendin–4 to Inhibit Pentagastrin–Stimulated Gastric Acid Secretion in Rats," *Gastroenterology,* 112(4):A194, (1997).

Miholic et al., "Glucagon–like (GLP–1), Entleerung des Magenersatzes und das Dumpingsyndrom nach Gastrektomie," *Chirurgishes Forum,* 1991, pp. 429–432 (English abstract and International Search Report in which the article is referenced are attached).

Nauck et al., "Effects of Subcutaneous Glucagon–like Peptide 1 (GLP–1 [7–36 Amide]) in Patients with Type 2–Diabetes," *Diabetologia,* Abstract A148, 38 Supp. 1:A39 (1995).

Orskov et al., "Is the Effect of Glucagon–like Peptide–1 on Gastric Emptying Centrally Mediated?", *Diabetologia,* Abstract A147, 38 Supp. 1:A39, (1995).

Ritzel et al., "GLP–1 [7–36 Amide] Augments Bisphasic Insulin Secretion After Intravenous Glucose in Healthy Volunteers," *Diabetologia,* Abstract A145, 38 Supp. 1:A39, (1995).

Navarro, M. et al., "Colocalization of Glucagon–Like Peptide–1 (GLP–1) Receptors, Glucose Transporter GLUT–2, and Glucokinase mRNAs in Rat Hypothalamic Cells: Evidence for a Role of GLP–1 Receptor Agonists as an Inhibitory Signal for Food and Water Intake," *Journal of Neurochemistry,* 67:1982–1991 (1996).

Daniel et al. "Use of Glucagon in the Treatment of Acute Diverticulitis," *Br. Med. J.,* 3:720, 1974.

D'Alessio et al. "Elimination of the Action of glucagon–like Peptide 1 Causes an Impairment of glucose tolerance after Nutrient Ingestion by Healthy Baboons," *J. Clin. Invest.,* 97:133–38, 1996.

Eissele et al. "Rat Gastric somatostatin and Gastrin Release: Interactions of Exendin–4 and Truncated Glucagon–Like Peptide–1 (GLP–1) Amide," *Life Sci.,* 55:629–34, 1994.

Eng et al. "Purification and Structure of Exendin–3, a New Pancreatic Secretagogue Isolated from *Heloderma horridum* Venom," *J. Biol. Chem.,* 265:20259–62, 1990.

(List continued on next page.)

*Primary Examiner*—Karen A. Canella
(74) *Attorney, Agent, or Firm*—Arnold & Porter LLP

(57) ABSTRACT

Methods for reducing gastric motility and delaying gastric emptying for therapeutic and diagnostic purposes are disclosed which comprise administration of an effective amount of an exendin or an exendin agonist. Methods for treating conditions associated with elevated, inappropriate, or undesired post-prandial blood glucose levels are disclosed which comprise administration of an effective amount of an exendin or an exendin agonist alone or in conjunction with other anti-gastric emptying agents.

22 Claims, 8 Drawing Sheets

OTHER PUBLICATIONS

Eng et al. "Isolation and Characterization of Exendin–4, an Exendin–3 Analogue, from *Heloderma suspectum* Venom", *J. Biol. Chem.,* 267:7402–05, 1992.

Fehmann et al. "Stable Expression of the Rat GLP–1 Receptor in CHO Cells: Activation and Binding Characteristics Utilizing GLP–I(7–36)–Amide, Oxyntomodulin, Exendin–4, and Exendin(9–39)," *Peptides* 15 (3): 453–6, 1994.

Ferguson et al. "Cell–Surface Anchoring of Proteins Via Glycosylphosphatidylinositol Structures", *Annu. Rev. Biochem.* 57:285–320, 1988.

Glauser et al. "Intravenous glucagon in the Management of Esophageal Food Obstruction", *J. Am. Coll. Emergency Physns,* 8:228, 1979.

Gedulin et al. "Comparison of Effects of Amylin, Glucagon–like Peptide–1 and Exendin–4 to Inhibit Pentagastrin–Stimulated Gastric Acid Secretion," *Diabetologia,* 40 (Suppl. 1):A300 (Abstract 1181) (1997) 8:228, 1979.

Goke et al. "Exendin–4 Is a High Potency Agonist and Truncated Exendin–(9–39)–amide an Antagonist at the Glucagon–like Peptide 1–(7–36)–amide Receptor of Insulin–secreting β–Cells", *J. Biol. Chem.,* 268:19650–55, 1993.

Kolligs et al. "Reduction of the Incretin effect in Rats by the Glucagon–Like Peptide 1 Receptor antagonist Exendin(9–39) Amide", *Diabetes*, 44:16–19, 1995.

Malhotra et al. "Exendin–4, a new peptide from *Heloderma suspectum* venom, potentiates cholecystokinin–induced amylase release from rat pancreatic acini", *Regulatory Peptides,* 41:149–56, 1992.

Montros–Rafizadeh et al. "Structure–function Analysis of Exendin–4 / GLP–1 Analogs", *Diabetes,* 45(Suppl. 2):152A, 1996.

O'Halloran et al. "Glucagon–like peptide–1 (7–36)–$NH_2$: a physiological inhibitor of gastric acid secretion in man," *J Endocrinol* 126 (1): 169–73, 1990.

Orskov et al. "Biological Effects and Metabolic Rates of Glucagonlike Peptide–1 7–36 Amide and glucagonlike Peptide–1 7–37 in Healthy Subjects Are Indistinguishable", *Diabetes,* 42:658–61, 1993.

Raufman et al. "Truncated Glucagon–like Peptide–1 Interacts with Exendin Receptors in Dispersed Acini from Guinea Pig Pancreas", *J. Biol. Chem.* 267:21432–37, 1992.

Raufman et al. "Exendin–3, a Novel Peptide from *Heloderma horridum* Venom, Interacts with Vasoactive Intestinal Peptide Receptors and a Newly Described Receptor on dispersed Acini from Guinea Pig Pancreas," *J. Biol. Chem.* 266:2897–902, 1991.

Scarpignato et al. "Action of Caerulein on gastric emptying of the Conscious Rat", *Arch. Int. Pharmacodyn. Ther.* 246:286–94 1980.

Schepp, et al. "Exendin–4 and exendin–(9–39)$NH_2$: agonist and antagonist, respectively, at the rat parietal cell receptor for glucagon–like peptide–1–(7–36)$NH_2$," *Eur. J. Pharm.* 269:183–91, 1994.

Schjoldager et al. "GLP–1 (Glucagon–like Peptide 1) and Truncated GLP–1, Fragments of Human Proglucagon, Inhibit Gastric Acid Secretion in Humans," *Dig. Dis Sci* 34 (5): 703–8, 1989.

Singh et al. "Use of $^{125}$I–[$Y^{39}$]exendin–4 to characterize exendin receptors on dispersed pancreatic acini and gastric chief cells from guinea pig," *Regul. Pept.* 53:47–59, 1994.

Stower et al. "A trial of glucagon in the treatment of painful biliary tract disease," *Br. J. Surg.,* 69:591–2, 1982.

Thorens et al. "Cloning and Functional Expression of the Human Islet GLP–1 Receptor," *Diabetes* 42 (11): 1678–82, 1993.

Thorens, "Expression cloning of the pancreatic β cell receptor for the gluco–incretin hormone glucagon–like peptide 1," *Proc. Natl. Acad. Sci. USA* 89:8641–45, 1992.

Wang et al. "Glucagon–like Peptide–1 Is a Physiological Incretin in Rat," *J. Clin. Invest.,* 95:417–21, 1995.

Wang, Y.J. and Hanson, M.A. "Parenteral Formulations of Proteins and Peptides: Stability and Stabilizers," *Journal of Parenteral Science and Technology,* Technical Report No. 10, Supp. 42:2S, 1988.

Wettergren et al. "Truncated GLP–1 (Proglucagon 78–107–Amide) Inhibits Gastric and Pancreatic Functions in Man," *Dig Dis Sci* 38 (4): 665–73, 1993.

Willms et al. "Gastric Emptying, Glucose Responses, and Insulin Secretion after a Liquid Test Mel: Effects of Exogenous Glucagon–Like Peptide–1 (GLP–1)–(7–36) Amide in Type 2 (Noninsulin–Dependent) Diabetic Patients," *J. Clin. Endocrinol. Metab.* 81(1):327–32 1996.

* cited by examiner

Glp-1 [SEQ.ID NO.3]

HAEGTFTSDV SSYLEGQAAK EFIAWLVKGR $NH_2$

Exendin-3 [SEQ.ID. NO.1]

HSDGTFTSDL SKQMEEEAVR LFIEWLKNGG PSSGAPPPS-$NH_2$

Exendin-4 [SEQ.ID NO.2]

HGEGTFTSDL SKQMEEEAVR LFIEWLKNGG PSSGAPPPS-$NH_2$

Exendin[9-39] [SEQ.ID NO.4]

DL SKQMEEEAVR LFIEWLKNGG PSSGAPPPS-$NH_2$

FIG. 1

1 $Xaa_1$ $Xaa_2$ $Xaa_3$ Gly 5 Thr $Xaa_4$ $Xaa_5$ $Xaa_6$ $Xaa_7$ 10 $Xaa_8$ Ser Lys Gln $Xaa_9$ 15 Glu Glu Glu Ala Val 20 Arg Leu $Xaa_{10}$ $Xaa_{11}$ $Xaa_{12}$ 25 $Xaa_{13}$ Leu Lys Asn Gly 30 Gly $Xaa_{14}$ Ser Ser Gly 35 Ala $Xaa_{15}$ $Xaa_{16}$ $Xaa_{17}$ $Xaa_{18}$ -Z

| Compound [SEQ.ID NO.] | $Xaa_1$ | $Xaa_2$ | $Xaa_3$ | $Xaa_4$ | $Xaa_5$ | $Xaa_6$ | $Xaa_7$ | $Xaa_8$ | $Xaa_9$ | $Xaa_{10}$ | $Xaa_{11}$ | $Xaa_{12}$ | $Xaa_{13}$ | $Xaa_{14}$ | $Xaa_{15}$ | $Xaa_{16}$ | $Xaa_{17}$ | $Xaa_{18}$ | Z |
|---|---|---|---|---|---|---|---|---|---|---|---|---|---|---|---|---|---|---|---|
| 1[5] | His | Gly | Glu | Phe | Thr | Ser | Asp | Leu | Leu | Phe | Ile | Glu | Phe | Pro | Pro | Pro | Pro | Ser | $NH_2$ |
| 2[6] | His | Gly | Glu | Phe | Thr | Ser | Asp | Leu | Leu | Phe | Ile | Glu | Trp | Pro | Pro | Pro | Pro | Ser | $NH_2$ |
| 3[7] | His | Gly | Glu | Phe | Thr | Ser | Asp | Leu | Met | Phe | Ile | Glu | Phe | Pro | Pro | Pro | Pro | Ser | $NH_2$ |
| 4[8] | Tyr | Gly | Glu | Phe | Thr | Ser | Asp | Leu | Met | Phe | Ile | Glu | Trp | Pro | Pro | Pro | Pro | Ser | $NH_2$ |
| 5[9] | His | Gly | Glu | Phe | Thr | Ser | Asp | Leu | Met | Phe | Ile | Glu | Trp | Pro | Pro | Pro | Pro | Tyr | $NH_2$ |
| 6[10] | His | Gly | Asp | Phe | Thr | Ser | Asp | Leu | Met | Phe | Ile | Glu | Trp | Pro | Pro | Pro | Pro | Ser | $NH_2$ |
| 7[11] | His | Gly | Glu | naph | Thr | Ser | Asp | Leu | Met | Phe | Ile | Glu | Trp | Pro | Pro | Pro | Pro | Ser | $NH_2$ |
| 8[12] | His | Gly | Glu | Phe | Ser | Ser | Asp | Leu | Met | Phe | Ile | Glu | Trp | Pro | Pro | Pro | Pro | Ser | $NH_2$ |
| 9[13] | His | Gly | Glu | Phe | Ser | Thr | Asp | Leu | Met | Phe | Ile | Glu | Trp | Pro | Pro | Pro | Pro | Ser | $NH_2$ |
| 10[14] | His | Gly | Glu | Phe | Thr | Thr | Asp | Leu | Met | Phe | Ile | Glu | Trp | Pro | Pro | Pro | Pro | Ser | $NH_2$ |
| 11[15] | His | Gly | Glu | Phe | Thr | Ser | Glu | Leu | Met | Phe | Ile | Glu | Trp | Pro | Pro | Pro | Pro | Ser | $NH_2$ |
| 12[16] | His | Gly | Glu | Phe | Thr | Ser | Asp | pGly | Met | Phe | Ile | Glu | Trp | Pro | Pro | Pro | Pro | Ser | $NH_2$ |
| 13[17] | His | Gly | Glu | Phe | Thr | Ser | Asp | pGly | Leu | Phe | Ile | Glu | Phe | Pro | Pro | Pro | Pro | Ser | $NH_2$ |
| 14[18] | His | Gly | Glu | Phe | Thr | Ser | Asp | Leu | pGly | Phe | Ile | Glu | Trp | Pro | Pro | Pro | Pro | Ser | $NH_2$ |

FIG. 8A

| Compound [SEQ.ID NO.] | $Xaa_1$ | $Xaa_2$ | $Xaa_3$ | $Xaa_4$ | $Xaa_5$ | $Xaa_6$ | $Xaa_7$ | $Xaa_8$ | $Xaa_9$ | $Xaa_{10}$ | $Xaa_{11}$ | $Xaa_{12}$ | $Xaa_{13}$ | $Xaa_{14}$ | $Xaa_{15}$ | $Xaa_{16}$ | $Xaa_{17}$ | $Xaa_{18}$ | Z |
|---|---|---|---|---|---|---|---|---|---|---|---|---|---|---|---|---|---|---|---|
| 15[19] | His | Gly | Glu | Phe | Thr | Ser | Asp | Leu | pGly | Phe | Ile | Glu | Phe | Pro | Pro | Pro | Pro | Ser | $NH_2$ |
| 16[20] | His | Gly | Glu | Phe | Thr | Ser | Asp | Leu | Met | naph | Ile | Glu | Trp | Pro | Pro | Pro | Pro | Ser | $NH_2$ |
| 17[21] | His | Gly | Glu | Phe | Thr | Ser | Asp | Leu | Met | Phe | Val | Glu | Trp | Pro | Pro | Pro | Pro | Ser | $NH_2$ |
| 18[22] | His | Gly | Glu | Phe | Thr | Ser | Asp | Leu | Leu | Phe | Val | Glu | Phe | Pro | Pro | Pro | Pro | Ser | $NH_2$ |
| 19[23] | His | Gly | Glu | Phe | Thr | Ser | Asp | Leu | Met | Phe | tBuG | Glu | Trp | Pro | Pro | Pro | Pro | Ser | $NH_2$ |
| 20[24] | His | Gly | Glu | Phe | Thr | Ser | Asp | Leu | Leu | Phe | tBuG | Glu | Phe | Pro | Pro | Pro | Pro | Ser | $NH_2$ |
| 21[25] | His | Gly | Glu | Phe | Thr | Ser | Asp | Leu | Met | Phe | Ile | Asp | Trp | Pro | Pro | Pro | Pro | Ser | $NH_2$ |
| 22[26] | His | Ala | Glu | Phe | Thr | Ser | Asp | Leu | Leu | Phe | Ile | Glu | Phe | Pro | Pro | Pro | Pro | Ser | $NH_2$ |
| 23[27] | His | Gly | Glu | Phe | Thr | Ser | Asp | Leu | Met | Phe | Ile | Glu | Trp | tPro | tPro | tPro | tPro | Ser | $NH_2$ |
| 24[28] | His | Gly | Glu | Phe | Thr | Ser | Asp | Leu | Met | Phe | Ile | Glu | Trp | Pro | tPro | tPro | tPro | Ser | $NH_2$ |
| 25[29] | His | Gly | Glu | Phe | Thr | Ser | Asp | Leu | Met | Phe | Ile | Glu | Trp | hPro | hPro | hPro | hPro | Ser | $NH_2$ |
| 26[30] | His | Gly | Glu | Phe | Thr | Ser | Asp | Leu | Met | Phe | Ile | Glu | Trp | Pro | hPro | hPro | hPro | Ser | $NH_2$ |
| 27[31] | His | Gly | Glu | Phe | Thr | Ser | Asp | Leu | Leu | Phe | Ile | Glu | Phe | tPro | tPro | tPro | tPro | Ser | $NH_2$ |
| 28[32] | His | Gly | Glu | Phe | Thr | Ser | Asp | Leu | Leu | Phe | Ile | Glu | Phe | hPro | hPro | hPro | hPro | Ser | $NH_2$ |
| 29[33] | His | Gly | Glu | Phe | Thr | Ser | Asp | Leu | Met | Phe | Ile | Glu | Trp | MeAla | MeAla | MeAla | MeAla | Ser | $NH_2$ |
| 30[34] | His | Gly | Glu | Phe | Thr | Ser | Asp | Leu | Met | Phe | Ile | Glu | Trp | Pro | MeAla | MeAla | MeAla | Ser | $NH_2$ |
| 31[35] | His | Gly | Glu | Phe | Thr | Ser | Asp | Leu | Leu | Phe | Ile | Glu | Phe | MeAla | MeAla | MeAla | MeAla | Ser | $NH_2$ |

FIG. 8B

SEQUENCE LISTING

```
(1) GENERAL INFORMATION:

   (iii) NUMBER OF SEQUENCES: 39


(2) INFORMATION FOR SEQ ID NO: 1:

     (i) SEQUENCE CHARACTERISTICS:
```

-continued (A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 1:

```
His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 2:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 2:

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 3:

(i) SEQUENCE CHARACTERISTICS:
(A) LENGTH: 30 amino acids
(B) TYPE: amino acid
(C) STRANDEDNESS: single
(D) TOPOLOGY: linear (ii) MOLECULE TYPE: peptide (ix) FEATURE:
(B) LOCATION: 30
(D) OTHER INFORMATION: amidated Arg (Arginineamide)

(xi) SEQUENCE DESCRIPTION: SEQ ID NO: 3:

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

(2) INFORMATION FOR SEQ ID NO: 4:

(i) SEQUENCE CHARACTERISTICS:
(A) LENGTH: 31 amino acids
(B) TYPE: amino acid
(C) STRANDEDNESS: single
(D) TOPOLOGY: linear -continued (ii) MOLECULE TYPE: peptide (ix) FEATURE:
(B) LOCATION: 31
(D) OTHER INFORMATION: amidated Ser (Serineamide)

(xi) SEQUENCE DESCRIPTION: SEQ ID NO: 4:

```
Asp Leu Ser Lys Gly Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

(2) INFORMATION FOR SEQ ID NO: 5:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 5:

```
His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

(2) INFORMATION FOR SEQ ID NO: 6:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 6:

```
His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 7:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:

-continued (B) LOCATION: 39
(D) OTHER INFORMATION: amidated Ser (Serineamide)

(xi) SEQUENCE DESCRIPTION: SEQ ID NO: 7:

```
His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

(2) INFORMATION FOR SEQ ID NO: 8:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 8:

```
Tyr Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 9:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Tyr (Tyrosinamide)

(xi) SEQUENCE DESCRIPTION: SEQ ID NO: 9:

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Tyr
        35
```

(2) INFORMATION FOR SEQ ID NO: 10:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39

-continued (D) OTHER INFORMATION: amidated Ser (Serineamide)

(xi) SEQUENCE DESCRIPTION: SEQ ID NO: 10:

```
His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 11:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 11:

```
His Gly Glu Gly Thr Ala Thr Ser Asp Leu Ser Lys Gln Met Glu Glu
1               5                    10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 12:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 12:

```
His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 13:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

-continued (xi) SEQUENCE DESCRIPTION: SEQ ID NO: 13:

```
His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 14:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 14:

```
His Gly Glu Gly Thr Phe Thr Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 15:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 15:

```
His Gly Glu Gly Thr Phe Thr Ser Glu Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 16:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

-continued (xi) SEQUENCE DESCRIPTION: SEQ ID NO: 16:

```
His Gly Glu Gly Thr Phe Thr Ser Asp Gly Ser Lys Gln Met Glu Glu
1               5                   10                  15

Glu Ala Val Arg Leu Met Ile Glu Trp Leu Lys Asn Gly Gly Pro Ser
            20                  25                  30

Ser Gly Ala Pro Pro Pro Ser
        35
```

(2) INFORMATION FOR SEQ ID NO: 17:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 17:

```
His Gly Glu Gly Thr Phe Thr Ser Asp Gly Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

(2) INFORMATION FOR SEQ ID NO: 18:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 18:

```
His Gly Glu Gly Thr Phe Thr Ser Asp Leu Ser Lys Gln Gly Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 19:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 19:

-continued

```
His Gly Glu Gly Thr Phe Thr Ser Asp Leu Ser Lys Gln Gly Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

(2) INFORMATION FOR SEQ ID NO: 20:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 20:

```
His Gly Glu Gly Thr Phe Thr Ser Asp Leu Ser Lys Gln Met Glu Glu
1               5                   10                  15

Glu Ala Val Arg Leu Ala Ile Glu Trp Leu Lys Asn Gly Gly Pro Ser
            20                  25                  30

Ser Gly Ala Pro Pro Pro Ser
        35
```

(2) INFORMATION FOR SEQ ID NO: 21:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 21:

```
His Gly Glu Gly Thr Phe Thr Ser Asp Leu Ser Lys Gln Met Glu Glu
1               5                   10                  15

Glu Ala Val Arg Leu Phe Val Glu Trp Leu Lys Asn Gly Gly Pro Ser
            20                  25                  30

Ser Gly Ala Pro Pro Pro Ser
        35
```

(2) INFORMATION FOR SEQ ID NO: 22:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 22:

-continued

His Gly Glu Gly Thr Phe Thr Ser Asp Leu Ser Lys Gln Leu Glu Glu
1 5 10 15

Glu Ala Val Arg Leu Phe Val Glu Phe Leu Lys Asn Gly Gly Pro Ser
20 25 30

Ser Gly Ala Pro Pro Pro Ser
35

(2) INFORMATION FOR SEQ ID NO: 23:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 23:

His Gly Glu Gly Thr Phe Thr Ser Asp Leu Ser Lys Gln Met Glu Glu
1 5 10 15

Glu Ala Val Arg Leu Phe Gly Glu Trp Leu Lys Asn Gly Gly Pro Ser
20 25 30

Ser Gly Ala Pro Pro Pro Ser
35

(2) INFORMATION FOR SEQ ID NO: 24:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 24:

His Gly Glu Gly Thr Phe Thr Ser Asp Leu Ser Lys Gln Leu Glu Glu
1 5 10 15

Glu Ala Val Arg Leu Phe Gly Glu Phe Leu Lys Asn Gly Gly Pro Ser
20 25 30

Ser Gly Ala Pro Pro Pro Ser
35

(2) INFORMATION FOR SEQ ID NO: 25:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 25:

His Gly Glu Gly Thr Phe Thr Ser Asp Leu Ser Lys Gln Met Glu Glu

-continued

```
1               5                   10                  15

Glu Ala Val Arg Leu Phe Ile Asp Trp Leu Lys Asn Gly Gly Pro Ser
            20                  25                  30

Ser Gly Ala Pro Pro Pro Ser
        35
```

(2) INFORMATION FOR SEQ ID NO: 26:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 26:

```
His Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

(2) INFORMATION FOR SEQ ID NO: 27

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 27:

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 28

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 28:

```
His Gly Glu Gly Thr Phe Thr Ser Asp Leu Ser Lys Gln Met Glu Glu
1               5                   10                  15
```

-continued

Glu Ala Val Arg Leu Phe Ile Glu Trp Leu Lys Asn Gly Gly Pro Ser
20 25 30

Ser Gly Ala Pro Pro Pro Ser
35

(2) INFORMATION FOR SEQ ID NO: 29

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 29:

His Gly Glu Gly Thr Phe Thr Ser Asp Leu Ser Lys Gln Met Glu Glu
1 5 10 15

Glu Ala Val Arg Leu Phe Ile Glu Trp Leu Lys Asn Gly Gly Pro Ser
20 25 30

Ser Gly Ala Pro Pro Pro Ser
35

(2) INFORMATION FOR SEQ ID NO: 30

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 30:

His Gly Glu Gly Thr Phe Thr Ser Asp Leu Ser Lys Gln Met Glu Glu
1 5 10 15

Glu Ala Val Arg Leu Phe Ile Glu Trp Leu Lys Asn Gly Gly Pro Ser
20 25 30

Ser Gly Ala Pro Pro Pro Ser
35

(2) INFORMATION FOR SEQ ID NO: 31

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 31:

His Gly Glu Gly Thr Phe Thr Ser Asp Leu Ser Lys Gln Leu Glu Glu
1 5 10 15

-continued

Glu Ala Val Arg Leu Phe Ile Glu Phe Leu Lys Asn Gly Gly Pro Ser
20 25 30

Ser Gly Ala Pro Pro Pro Ser
35

(2) INFORMATION FOR SEQ ID NO: 32

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 32:

His Gly Glu Gly Thr Phe Thr Ser Asp Leu Ser Lys Gln Leu Glu Glu
1 5 10 15

Glu Ala Val Arg Leu Phe Ile Glu Phe Leu Lys Asn Gly Gly Pro Ser
20 25 30

Ser Gly Ala Pro Pro Pro Ser
35

(2) INFORMATION FOR SEQ ID NO: 33

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 33:

His Gly Glu Gly Thr Phe Thr Ser Asp Leu Ser Lys Gln Met Glu Glu
1 5 10 15

Glu Ala Val Arg Leu Phe Ile Glu Trp Leu Lys Asn Gly Gly Ala Ser
20 25 30

Ser Gly Ala Ala Ala Ala Ser
35

(2) INFORMATION FOR SEQ ID NO: 34

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 34:

His Gly Glu Gly Thr Phe Thr Ser Asp Leu Ser Lys Gln Met Glu Glu
1 5 10 15

Glu Ala Val Arg Leu Phe Ile Glu Trp Leu Lys Asn Gly Gly Pro Ser

-continued

```
            20                  25                  30

Ser Gly Ala Ala Ala Ala Ser
        35
```

(2) INFORMATION FOR SEQ ID NO: 35

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (ix) FEATURE:
(B) LOCATION: 39
(D) OTHER INFORMATION: amidated Ser (Serineamide)

(xi) SEQUENCE DESCRIPTION: SEQ ID NO: 35:

```
His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Ala Ser
            20                  25                  30

Ser Gly Ala Ala Ala Ala Ser
        35
```

(2) INFORMATION FOR SEQ ID NO: 36

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 36:

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

(2) INFORMATION FOR SEQ ID NO: 37

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 37:

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

(2) INFORMATION FOR SEQ ID NO: 38:

(i) SEQUENCE CHARACTERISTICS:
(A) LENGTH: 40 amino acids
(B) TYPE: amino acid
(C) STRANDEDNESS: single -continued

```
        (D) TOPOLOGY: linear

   (ii) MOLECULE TYPE: peptide

   (ix) FEATURE:
        (B) LOCATION: 8, 9, 10 AND 14
        (D) OTHER INFORMATION: Xaa in position 8 is Ser or Thr; Xaa in
            position 9 is Asp or Glu; Xaa in position 10 is Leu, Ile,
            Val, pentylglycine or Met; Xaa in position 14 is Leu, Ile,
            pentylglycine, Val or Met;

   (xi) SEQUENCE DESCRIPTION: SEQ ID NO: 38:

 Xaa Xaa Xaa Gly Thr Xaa Xaa Xaa Xaa Xaa Ser Lys Gln Xaa Glu Glu
  1               5                  10                  15

 Glu Ala Val Arg Leu Xaa Xaa Xaa Xaa Leu Lys Asn Gly Gly Xaa Ser
             20                  25                  30

 Ser Gly Ala Xaa Xaa Xaa Xaa Xaa
         35                  40


(2) INFORMATION FOR SEQ ID NO: 39:

    (i) SEQUENCE CHARACTERISTICS:
        (A) LENGTH: 40 amino acids
        (B) TYPE: amino acid
        (C) STRANDEDNESS: single
        (D) TOPOLOGY: linear

   (ii) MOLECULE TYPE: peptide

   (ix) FEATURE:
        (B) LOCATION: 8, 9, 10, 14 AND 22
        (D) OTHER INFORMATION: Xaa in position 8 is Ser or Thr; Xaa in
            position 9 is Asp or Glu; Xaa in position 10 is Leu or
            pentylglycine; Xaa in position 14 is Leu or pentylglycine;
            Xaa in position 22 is Phe or naphthylalanine;

   (xi) SEQUENCE DESCRIPTION: SEQ ID NO: 39:

 Xaa Xaa Xaa Gly Thr Xaa Xaa Xaa Xaa Xaa Ser Lys Gln Xaa Glu Glu
  1               5                  10                  15

 Glu Ala Val Arg Leu Xaa Xaa Xaa Xaa Leu Lys Asn Gly Gly Xaa Ser
             20                  25                  30

 Ser Gly Ala Xaa Xaa Xaa Xaa Xaa
         35                  40
```

METHODS FOR REGULATING GASTROINTESTINAL MOTILITY

RELATED APPLICATION

This application is continuation-in-part of U.S. patent application Ser. No. 08/694,954 filed Aug. 8, 1996 now abandoned, the contents of which are hereby incorporated by this reference.

FIELD OF THE INVENTION

The present invention relates to methods for regulating gastrointestinal motility. More particularly, the invention relates to the use of exendins and analogs and agonists thereof for the treatment of disorders which would be benefited with agents useful in delaying and/or slowing gastric emptying.

BACKGROUND

The following description includes information that may be useful in understanding the present invention. It is not an admission that any of the information provided herein is prior art to the presently claimed invention, nor that any of the publications specifically or implicitly referenced are prior art to that invention.

Publications and other materials including patents and patent applications used to illuminate the specification are hereby incorporated by reference.

Exendin

The exendins are peptides that are found in the venom of the Gila-monster, a lizard found in Arizona. Exendin-3 [SEQ. ID. NO. 1] is present in the venom of *Heloderma horridum*, and exendin-4 [SEQ. ID. NO. 2] is present in the venom of *Heloderma suspectum* (Eng, J., et al., *J. Biol. Chem.*, 265:20259–62, 1990; Eng., J., et al., *J. Biol. Chem.*, 267:7402–05, 1992). The exendins have some sequence similarity: to several members of the glucagon-like peptide family, with the highest homology, 53%, being to GLP-1 [7–36]$NH_2$ (Goke, et al., *J. Biol. Chem.*, 268:19650–55, 1993). GLP-1 [7–36]$NH_2$ [SEQ. ID. NO. 3] is also known as proglucagon [78–107], or simply the shorthand "GLP-1," which is used interchangeably with GLP-1 [7–36]$NH_2$ throughout this application. The sequences of exendin-3, exendin-4 and GLP-1 are shown in FIG. 1. GLP-1 has an insulinotropic effect, stimulating insulin secretion from pancreatic β-cells; GLP-1 also inhibits glucagon secretion from pancreatic α-cells (Ørskov, et al., *Diabetes*, 42:658–61, 1993; D'Alessio, et al., *J. Clin. Invest.*, 97:133–38, 1996). GLP-1 is reported to inhibit gastric emptying (Willms B, et al., *J. Clin Endocrinol Metab* 81 (1): 327–32, 1996; Wettergren A, et al., *Dig Dis Sci* 38 (4): 665–73, 1993), and gastric acid secretion. Schjoldager B T, et al., *Dig Dis Sci* 34 (5): 703–8, 1989; O'Halloran D J, et al., *J Endocrinol* 126 (1): 169–73, 1990; Wettergren A, et al., *Dig Dis sci* 38 (4): 665–73, 1993). GLP-1 [7–37], [SEQ. ID. NO. 37] which has an additional glycine residue at its carboxy terminus, also stimulates insulin secretion in humans (Ørskov, et al., *Diabetes*, 42:658–61, 1993).

A transmembrane G-protein adenylate-cyclase-coupled receptor believed to be responsible for the insulinotropic effect of GLP-1 has been cloned from a β-cell line (Thorens, Proc. Natl. Acad. Sci. USA 89:8641–45 (1992), hereinafter referred to as the "cloned GLP-1 receptor." Exendin-4 is reportedly a potent agonist at GLP-1 receptors on insulin-secreting βTC1 cells, at dispersed acinar cells from guinea pig pancreas, and at parietal cells from stomach; the peptide is also reported to stimulate somatostatin release and inhibit gastrin release in isolated stomachs (Goke, et al., *J. Biol. Chem.* 268:19650–55, 1993; Schepp, et al., *Eur. J. Pharmacol*, 69:183–91, 1994; Eissele, et al., *Life Sci.*, 55:629–34, 1994). Exendin-3 and exendin-4 were found to be GLP-1 agonists in stimulating cAMP production in, and amylase release from, pancreatic acinar cells (Malhotra, R., et al., *Regulatory Peptides*, 41:149–56, 1992; Raufman, et al., *J. Biol. Chem.* 267:21432–37, 1992; Singh, et al., *Regul. Pept.* 53:47–59, 1994). Based on the insulinotropic activities of exendin-3 and exendin-4, their use has been proposed for the treatment of diabetes mellitus and the prevention of hyperglycemia (Eng, U.S. Pat. No. 5,424,286).

In contrast to the full-length exendins, truncated exendin peptides such as exendin [9–39], [SEQ. ID. NO. 4] a carboxyamidated molecule, and fragments 3–39 through 9–39 of exendin have been reported to be potent and selective antagonists of GLP-1 (Goke, et al., *J. Biol. Chem.*, 268:19650–55, 1993; Schepp, W., et al., *Eur. J. Pharm.* 269:183–91, 1994; Montrose-Rafizadeh, et al., *Diabetes*,45 (Suppl. 2):152A, 1996). Exendin [9–39], the sequence of which is shown in FIG. 1, reportedly blocks endogenous GLP-1 in vivo, resulting in reduced insulin secretion. Wang, et al., *J. Clin. Invest.*, 95:417–21, 1995; D'Alessio, et al., *J. Clin. Invest.*, 97:133–38, 1996). Exendins and exendin [9–391] bind to the cloned GLP-1 receptor (Fehmann H C, et al., Peptides 15 (3): 453–6, 1994; Thorens B, et al., *Diabetes* 42 (11): 1678–82, 1993). In cells transfected with the cloned GLP-1 receptor, exendin-4 is an agonist, i.e., it increases cAMP, while exendin [9–39] is an antagonist, i.e., it blocks the stimulatory actions of exendin-4 and GLP-1.

Exendin [9–39] is also reported to act as an antagonist of the full length exendins, inhibiting stimulation of pancreatic acinar cells by exendin 3 and exendin 4 (Raufman, et al., *J. Biol. Chem.* 266:2897–902, 1991; Raufman, et al., *J. Biol. Chem.*, 266:21432–37, 1992). Exendin [9–39] is said to inhibit the stimulation of plasma insulin levels by exendin 4, and inhibits the somatostatin release-stimulating and gastrin release-inhibiting activities of exendin-4 and GLP-1 (Kolligs, F., et al., *Diabetes*, 44:16–19, 1995; Eissele, et al., *Life Sciences*, 55:629–34, 1994).

Agents which serve to delay gastric emptying have found a place in medicine as diagnostic aids in gastro-intestinal radiologic examinations. For example, glucagon is a polypeptide hormone which is produced by the a cells of the pancreatic islets of Langerhans. It is a hyperglycaemic agent which mobilizes glucose by activating hepatic glycogenolysis. It can to a lesser extent stimulate the secretion of pancreatic insulin. Glucagon is used in the treatment of insulin-induced hypoglycaemia when administration of glucose intravenously is not possible. However, as glucagon reduces the motility of the gastro-intestinal tract it is also used as a diagnostic aid in gastro-intestinal radiological examinations. Glucagon has also been used in several studies to treat various painful gastro-intestinal disorders associated with spasm. Daniel, et al. (Br. Med. J., 1974, 3, 720) reported quicker symptomatic relief of acute diverticulitis in patients treated with glucagon compared with those who had been treated with analgesics or antispasmodics. A review by Glauser, et al., (*J. Am. Coll. Emergency Physns*, 8:228, 1979) described relief of acute oesophageal food obstruction following glucagon therapy. In another study glucagon significantly relieved pain and tenderness in 21 patients with biliary tract disease compared with 22 patients treated with placebo (M. J. Stower, et al., Br. J. Surg, 69:591–2, 1982).

Methods for regulating gastrointestinal motility using amylin agonists are described in International Application No. PCT/US94/10225, published Mar. 16, 1995.

SUMMARY OF THE INVENTION

The present invention concerns the surprising discovery that exendins are potent inhibitors of gastric emptying. Exendins and exendin agonists are useful as inhibitors of gastric emptying for the treatment of, for example, diabetes mellitus, obesity, the ingestion of toxins, or for diagnostic purposes.

The present invention is directed to novel methods for reducing gastric motility and slowing gastric emptying, comprising the administration of an exendin, for example, exendin 3 [SEQ ID NO. 1], exendin 4 [SEQ ID NO. 2], or other compounds which effectively bind to the receptor at which exendins exert their action on gastric motility and gastric emptying. These methods will be useful in the treatment of, for example, post-prandial hyperglycemia, a complication associated with type 1 (insulin dependent) and type 2 (non-insulin dependent) diabetes mellitus.

In a first aspect, the invention features a method of beneficially regulating gastrointestinal motility in a subject by administering to said subject a therapeutically effective amount of an exendin or an exendin agonist. By "exendin agonist" is meant a compound which mimics the effects of exendins on gastric motility and gastric emptying, namely, a compound which effectively binds to the receptor at which exendins exert their action on gastric motility and gastric emptying, preferably an analog or derivative of an exendin.

Exendin agonist compounds useful in present invention include those compounds of the formula (I)

```
1                    5                        10
Xaa1 Xaa2 Xaa3 Gly Thr Xaa4 Xaa5 Xaa6 Xaa7 Xaa8

                15                  20
Ser Lys Gln Xaa9 Glu Glu Glu Ala Val Arg Leu

                25                  30
Xaa10 Xaa11 Xaa12 Xaa13 Leu Lys Asn Gly Gly Xaa14

            35
Ser Ser Gly Ala Xaa15 Xaa16 Xaa17 Xaa18-Z
```

wherein $Xaa_1$ is His, Arg or Tyr; $Xaa_2$ is Ser, Gly, Ala or Thr; $Xaa_3$ is Asp or $Glu_4$; Xaa is Phe, Tyr or naphthalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —$NH_2$; with the proviso that the compound does not have the formula of either SEQ. ID. NOS. 1 or 2. Also useful in the present invention are pharmaceutically acceptable salts of the compounds of formula (I).

In one embodiment, the methods of the present invention are directed to reducing gastric motility. In another embodiment, the invention is directed to methods of delaying gastric emptying.

These methods may be used on a subject undergoing a gastrointestinal diagnostic procedure, for example radiological examination or magnetic resonance imaging. Alternatively, these methods may be used to reduce gastric motility in a subject suffering from a gastrointestinal disorder, for example, spasm (which may be associated with acute diverticulitis, a disorder of the biliary tract or a disorder of the Sphincter of Oddi).

In another aspect, the invention is directed to a method of treating post-prandial dumping syndrome in a subject by administering to the subject a therapeutically effective amount of an exendin or exendin agonist.

In yet another aspect, the invention is directed to a method of treating post-prandial hyperglycemia by administering to a subject a therapeutically effective amount of an exendin or exendin agonist. In a preferred embodiment, the post-prandial hyperglycemia is a consequence of Type 2 diabetes mellitus. In other preferred embodiments, the post-prandial hyperglycemia is a consequence of Type 1 diabetes mellitus or impaired glucose tolerance.

In another aspect, a therapeutically effective amount of an amylin agonist is also administered to the subject. In a preferred aspect, the amylin agonist is an amylin or an amylin agonist analog such as $^{25,28,29}$Pro-human-amylin. The use of amylin agonists to treat post-prandial hyperglycemia, as well as to beneficially regulate gastrointestinal motility, is described in International Application No. PCT/US94/10225, published Mar. 16, 1995 which has been incorporated by reference herein.

In yet another aspect, a therapeutically effective amount of an insulin or insulin analog is also administered, separately or together with an exendin or exendin agonist, to the subject.

In another aspect, the invention is directed to a method of treating ingestion of a toxin by administering an amount of an exendin or an exendin agonist effective to prevent or reduce passage of stomach contents to the intestines and aspirating the stomach contents.

Definitions

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue, refers to radicals having the structure: (1) —C(O)—R—NH—, wherein R typically is —CH(R')—, wherein R' is an amino acid side chain, typically H or a carbon containing substitutent; or (2), wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

In addition, the following abbreviations stand for the following:

"ACN" or "$CH_3CN$" refers to acetonitrile.

"Boc", "tBoc" or "Tboc" refers to t-butoxy carbonyl.

"DCC" refers to N,N'-dicyclohexylcarbodiimide.

"Fmoc" refers to fluorenylmethoxycarbonyl.

"HBTU" refers to 2-(1H-benzotriazol-1-yl)-1,1,3,3,-tetramethyluronium hexaflurophosphate.

"HOBt" refers to 1-hydroxybenzotriazole monohydrate.

"homoP" or hPro" refers to homoproline.

"MeAla" or "Nme" refers to N-methylalanine.

"naph" rekgers to naphthylalanine.

"pG" or pGly refers to pentylglycine.

"tBuG" refers to tertiary-butylglycine.

"ThioP" or tpro" refers to thioproline.

BRIEF DESCRIPTION OF THE DRAWINGS

FIG. 1 shows a comparison of the amino acid sequences of GLP-1, exendin-3, exendin4 and exendin [9–39] using standard single letter rather than three letter amino acid codes.

As shown in FIG. 4, exendin-4 alone potently inhibited gastric emptying. Exendin [9–39] (sc) alone had no effect on gastric emptying. When injected along with exendin-4, exendin [9–39] did not antagonize the effect of exendin-4 on gastric emptying inhibition.

As shown in FIG. 5, exendin-4 alone potently inhibited gastric emptying. When injected along with exendin-4, exendin [9–39] (iv) did not antagonize the effect of exendin-4 on gastric emptying inhibition.

As shown in FIG. 6, GLP-1 [7–36]$NH_2$ potently inhibited gastric emptying. Exendin [9–39] (sc) alone had no effect on gastric emptying. When injected along with GLP-1 [7–36]$NH_2$, exendin [9–39] did not antagonize the effect of GLP-1 [7–36]$NH_2$ on gastric emptying inhibition.

As shown in FIG. 7, GLP-1 [7–36]NH2 alone potently inhibited gastric emptying. When injected along with GLP-1 [7–36]$NH_2$, exendin [9–39] (iv) did not antagonize the effect of GLP-1 [7–36]$NH_2$ on gastric emptying inhibition.

FIGS. 8A and 8B depict the amino acid sequences for certain exendin agonists [SEQ. ID. NOS. 5 TO 35].

DETAILED DESCRIPTION OF THE INVENTION

Figure 2:
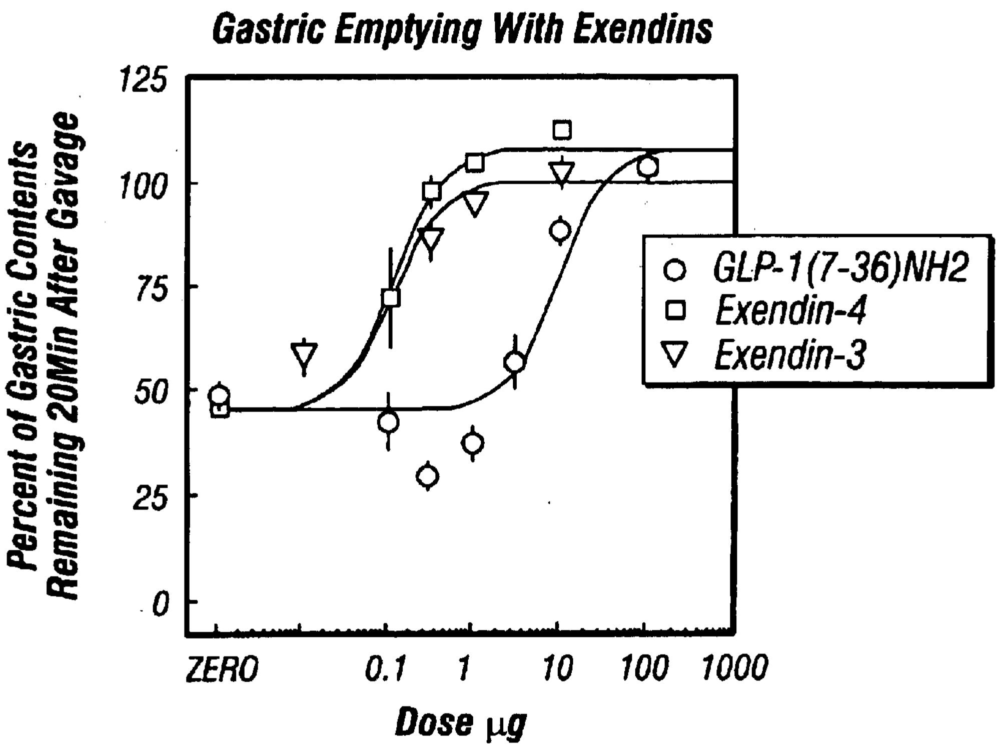
FIG. 2 shows GLP-1 [7–36]$NH_2$, exendin-3 and exendin-4 dose-response effects of prior subcutaneous injection on the retention of gastric contents 20 minutes after gavage in normal rats (n=3–17 for each point). Symbols are means±SEM and the curves define the best fitting logistic functions. "Zero" indicates the fraction of gastric contents retained in untreated normal rats.

Exendins and exendin agonists (including exendin analogs and exendin derivatives) are useful in this invention in view of their pharmacological properties. Activity as exendin agonists can be indicated by activity in the assays described below. Effects of exendins or exendin agonists on gastric motility and gastric emptying can be identified, evaluated, or screened for, using the methods described in Examples 1–3 below, or other art-known or equivalent methods for determining gastric motility. Negative receptor assays or screens for exendin agonist compounds or candidate exendin agonist compounds, such as a GLP-1 receptor preparation, an amylin receptor assay/screen using an amylin receptor preparation as described in U.S. Pat. No. 5,264,372, issued Nov. 23, 1993, the contents of which are incorporated herein by reference, one or more calcitonin receptor assays/screens using, for example, T47D and MCF7 breast carcinoma cells, which contain calcium receptors coupled to the stimulation of adenyl cyclase activity, and/or a CGRP receptor assay/screen using, for example, SK-N-MC cells, can be used to evaluate and/or confirm exendin agonist activity.

One such method for use in identifying or evaluating the ability of a compound to slow gastric motility, comprises: (a)

bringing together a test sample and a test system, said test sample comprising one or more test compounds, said test system comprising a system for evaluating gastric motility, said system being characterized in that it exhibits, for example, elevated plasma glucose in response to the introduction to said system of glucose or a meal; and, (b) determining the presence or amount of a rise in plasma glucose in said system. Positive and/or negative controls may be used as well.

Exendins and exendin agonist compounds such as exendin analogs and exendin derivatives, described herein may be prepared through peptide purification as described in, for example, Eng, et al., *J. Biol. Chem.* 265:20259–62, 1990; and Eng, et al., *J. Biol. Chem.* 267:7402–05, 1992, hereby incorporated by reference herein. Alternatively, exendins and exendin agonist peptides may be prepared by methods known to those skilled in the art, for example, as described in Raufman, et al. *J. Biol. Chem.* 267;21432–37, 1992), hereby incorporated by reference herein, using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The side-chain protected amino acids, such as Boc-Arg(Mts), Fmoc-Arg(Pmc), Boc-Thr(Bzl), Fmoc-Thr(t-Bu), Boc-Ser(Bzl) Fmoc-Ser(t-Bu), Boc-Tyr (BrZ), Fmoc-Tyr(t-Bu), Boc-Lys(Cl-Z), Fmoc-Lys(Boc), Boc-Glu(Bzl), Fmoc-Glu(t-Bu), Fmoc-His(Trt), Fmoc-Asn (Trt), and Fmoc-Gln(Trt) may be purchased from Applied Biosystems, Inc. Boc-His(BOM) may be purchased from Applied Biosystems, Inc. or Bachem Inc. (Torrance, Calif.). Anisole, methylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also assembled using an Advanced Chem Tech Synthesizer (Model MPS 350, Louisville, Ky.). Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac) Solvents (A=0.1% TFA/water and B=0.1% TFA/$CH_3CN$) may be delivered to the analytical column at a flowrate of 1.0 ml/min and to the preparative column at 15 ml/min. Amino acid analyses may be performed on the Waters Pico Tag system and processed using the Maxima program. The peptides may be hydrolyzed by vapor-phase acid hydrolysis (115° C., 20–24 h). Hydrolysates may be derivatized and analyzed by standard methods (Cohen, S. A., Meys, M., and Tarrin, T. L. (1989), *The Pico Tag Method: A Manual of Advanced Techniques for Amino Acid Analysis*, pp. 11–52, millipore Corporation, Milford, Mass.). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Peptide compounds useful in the invention may also be prepared using recombinant DNA techniques, using methods now known in the art. See, e.g., Sambrook, et al., *Molecular Cloning: A Laboratory Manual*, 2d Ed., Cold Spring Harbor (1989). Alternatively, such compounds may be prepared by homogeneous phase peptide synthesis methods.

The use of exendin analogs or derivatives is included within the methods of the present invention. Exendin analogs or derivatives are functional variants having similar amino acid sequence and retaining, to some extent, at least the gastric motility- and gastric emptying-related activities of the related exendin. By "functional variant" is meant an analog or derivative which has an activity that can be substituted for one or more activities of a particular exendin. Preferred functional variants retain all of the activities of a particular exendin, however, the functional variant may have an activity that, when measured quantitatively, is stronger or weaker, as measured in exendin functional assays, for example, such as those disclosed herein. Preferred functional variants have activities that are within about 1% to about 10,000% of the activity of the related exendin, more preferably between about 10% to about 1000%, and more preferably within about 50% to about 500%. Derivatives have at least about 15% sequence similarity, preferably about 70%, more preferably about 90%, and even more preferably about 95% sequence similarity to the related exendin. "Sequence similarity" refers to "homology" observed between amino acid sequences in two different polypeptides, irrespective of polypeptide origin.

The ability of the analog or derivative to retain some activity can be measured using techniques described herein.

Derivatives include modification occurring during or after translation, for example, by phosphorylation, glycosylation, crosslinking, acylation, proteolytic cleavage, linkage to an antibody molecule, membrane molecule or other ligand (see Ferguson et al., *Annu. Rev. Biochem.* 57:285–320, 1988).

Specific types of analogs include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Analogs can contain different combinations of alterations including more than one alteration and different types of alterations.

Preferred analogs have one or more amino acid alteration(s) which do not significantly affect exendin agonist activity. In regions of the exendin not necessary for exendin agonist activity, amino acids may be deleted, added or substituted with less risk of affecting activity. In regions required for exendin agonist activity, amino acid alterations are less preferred as there is a greater risk of affecting exendin activity. Such alterations should be conservative alterations. For example, one or more amino acid residues within the sequence can be substituted by another amino acid of a similar polarity which acts as a functional variant.

Conserved regions tend to be more important for protein activity than non-conserved regions. Known procedures may be used to determine the conserved and non-conserved regions important of receptor activity using in vitro mutagenesis techniques or deletion analyses and measuring receptor activity as described by the present disclosure.

Modifications to a specific polypeptide may be deliberate, as through site-directed mutagenesis and amino acid substitution during solid-phase synthesis, or may be accidental such as through mutations in hosts or systems which produce the polypeptide.

Compounds particularly useful according to the present invention are exendin agonist compounds of the formula (I):

```
1                    5                        10
Xaa1 Xaa2 Xaa3 Gly Thr Xaa4 Xaa5 Xaa6 Xaa7 Xaa8

                  15                     20
Ser Lys Gln Xaa9 Glu Glu Glu Ala Val Arg Leu

                   25                   30
Xaa10 Xaa11 Xaa12 Xaa13 Leu Lys Asn Gly Gly Xaa14

             35
Ser Ser Gly Ala Xaa15 Xaa16 Xaa17 Xaa18-Z
```

wherein $Xaa_1$ is His, Arg or Tyr; $Xaa_2$ is Ser, Gly, Ala or Thr, $Xaa_3$ is Asp or Glu; $Xaa_4$ is Phe, Tyr or naphthylalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —$NH_2$; with the proviso that the compound does not have the formula of either SEQ. ID. NOS. 1 or 2. Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds include those having amino acid sequences of SEQ. ID. NOS. 5 to 35.

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_9$ is Leu, pentylglycine or Met.

Preferred compounds include those wherein $Xaa_{13}$ is Trp or Phe.

Also preferred are compounds where $Xaa_4$ is Phe or naphthalanine; $Xaa_{11}$ is Ile or Val and $Xaa_{14}$, $Xaa_{15}$, $Xaa_{16}$ and $Xaa_{17}$ are independently selected from Pro, homoproline, thioproline or N-alkylalanine. Preferably N-alkylalanine has a N-alkyl group of 1 to about 6 carbon atoms.

According to an especially preferred aspect, $Xaa_{15}$, $Xaa_{16}$ and $Xaa_{17}$ are the same amino acid reside.

Preferred are compounds wherein $Xaa_{18}$ is Ser or Tyr, more preferably Ser.

Preferably Z is —$NH_2$.

According to one aspect, preferred are compounds of formula (I) wherein $Xaa_1$ is His or Tyr, more preferably His; $Xaa_2$ is Gly; $Xaa_4$ is Phe or naphthalanine; $Xaa_9$ is Leu, pentylglycine or Met; $Xaa_{10}$ is Phe or naphthalanine; $Xaa_{11}$ is Ile or Val; $Xaa_{14}$, $Xaa_{15}$, $Xaa_{16}$ and $Xaa_{17}$ are independently selected from Pro, homoproline, thioproline or N-alkylalanine; and $Xaa_{18}$ is Ser or Tyr, more preferably Ser. More preferably Z is —$NH_2$.

According to an especially preferred aspect, especially preferred compounds include those of formula (I) wherein: $Xaa_1$ is His or Arg; $Xaa_2$ is Gly; $Xaa_3$ is Asp or Glu; $Xaa_4$ is Phe or napthylalanine; $Xaa_5$ is Thr or Ser;

$Xaa_6$ is Ser or Thr; $Xaa_7$ is Asp or Glu; $Xaa_6$ is Leu or pentylglycine; $Xaa_9$ is Leu or pentylglycine; $Xaa_{10}$ is Phe or naphthylalanine; $Xaa_{11}$ is Ile, Val or t-butyltylglycine; $Xaa_{12}$ is Glu or Asp; $Xaa_{13}$ is Trp or Phe;

$Xaa_{14}$, $Xaa_{15}$, $Xaa_{16}$, and $Xaa_{17}$ are independently Pro, homoproline, thioproline, or N-methylalanine; $Xaa_{18}$ is Ser or Tyr: and Z is —OH or —$NH_2$; with the proviso that the compound does not have the formula of either SEQ. ID. NOS. 1 or 2. More preferably Z is —$NH_2$. Especially preferred compounds include those having the amino acid sequence of SEQ. ID. NOS. 5, 6, 17, 18, 19, 22, 24, 31, 32 and 35.

According to an especially preferred aspect, provided are compounds where $Xaa_9$ is Leu, Ile, Val or pentylglycine, more preferably Leu or pentylglycine, and $Xaa_{13}$ is Phe, Tyr or naphthylalanine, more preferably Phe or naphthylalanine. These compounds are believed to exhibit advantageous duration of action and to be less subject to oxidative degration, both in vitro and in vivo, as well as during synthesis of the compound.

The compounds referenced above form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds referenced above form salts with various inorganic and organic acids and bases. Such salts include salts prepared with organic and inorganic acids, for example, HCl , HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds described above are useful in view of their pharmacological properties. In particular, the compounds of the invention possess activity as agents to regulate gastric motility and to slow gastric emptying, as evidenced by the ability to inhibit gastric emptying levels in mammals.

As described in Example 1, gastric emptying was measured in normal Sprague Dawley rats using the retention of an acaloric methylcellulose gel containing Phenol Red delivered by gavage. Dye content in stomachs removed after sacrifice 20 minutes later was determined spectroscopically, and was compared to that in rats sacrificed immediately after gavage to assess emptying. The exendins, exendin 3 and exendin 4, dose-dependently inhibited gastric emptying. The $ED_{50}$ of the response to exendin 3 and exendin 4 was 0.1 and 0.08 $\mu$g, respectively, demonstrating that the exendins were ~170–290 times more I potent than GLP-1 [7–36]$NH_2$ in inhibiting gastric emptying.

As described in Example 2, the effects of exendin-4 and the exendin-4 analogs, exendin-4 acid and $^{14}$Leu,$^{25}$Phe exendin-4, on inhibition of gastric emptying were examined. Exendin-4 and the exendin-4 analogs dose dependently inhibiting gastric emptying. The $ED_{50}$ of exendin-4 was 0.27 $\mu$g. The ED,s of exendin-4 acid and $^{14}$Leu,$^{25}$Phe exendin-4 were 0.12 $\mu$g and 0.29 $\mu$g, respectively, indicating that the potency of the analogs was comparable to that of exendin-4.

As described in Example 3, the effects of exendin-4 and the cloned GLP-1 receptor antagonist, exendin [9–39] on gastric emptying were examined. After 20 minutes, the animals treated with exendin-4 showed potent inhibition of gastric emptying, which was not reversed by exendin [9–39]. This occurred regardless of whether the exendin [9–39] was administered sc or iv. Exendin [9–39] alone had no effect on gastric emptying.

As noted above, exendin [9–39] is a potent antagonist of GLP-1 which binds at the cloned GLP-1 receptor (Fehmann H C, et al., *Peptides* 15(3): 453–6, 1994; Thorens B, et al., *Diabetes* 42(11): 1678–82, 1993). Surprisingly, however, exendin [9–39] did not block the effect of exendin-4 on gastric emptying (see FIGS. 4 and 5). These results indicate that the effects of exendins and exendin agonists on gastric emptying are not due binding of the exendins at the cloned GLP-1 receptor, but instead that the gastric emptying effects of exendins and exendin agonists are due to their action on a separate receptor.

That exendins can act via mechanisms other than those attributable to the cloned GLP-l receptor is further evidenced by the reported absence of effect of exendin-4 on inhibition of pentagastrin-induced gastric acid secretion, despite the inhibitory effect of GLP-1 on such secretion. Gedulin, et al., *Diabetologia,* 40(Suppl. 1):A300 (Abstract 1181) (1997). Additionally, as described in commonly assigned U.S. Provisional Patent Application Ser. No. 60/034,905, entitled, "Use of Exendins and Agonists Therefor for the Reduction of Food Intake," filed Jan. 7, 1997, peripherally injected exendin inhibited food intake in mice, an action not observed with GLP-1.

Compositions useful in the invention may conveniently be provided in the form of formulations suitable for parenteral (including intravenous, intramuscular and subcutaneous) or nasal or oral administration. In some cases, it will be convenient to provide an exendin or exendin agonist and another anti-emptying agent, such as glucagon, or amylin, or an amylin agonist, in a single composition or solution for administration together. In other cases, it may be more advantageous to administer another anti-emptying agent separately from said exendin or exendin agonist. A suitable administration format may best be determined by a medical practitioner for each patient individually. Suitable pharmaceutically acceptable carriers and their formulation are described in standard formulation treatises, e.g., *Remington's Pharmaceutial Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an exendin or exendin agonist, for example, exendin 3, exendin 4, with or without another antiemptying agent. Therapeutically effective amounts of an exendin or exendin agonist for use in the control of gastric emptying and in conditions in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels, may be obtained. As will be recognized by those in the field, an effective amount of therapeutic agent will vary with many factors including the age and weight of the patient, the patient's physical condition, the blood sugar level or level of inhibition of gastric emptying to be obtained, and other factors.

Such pharmaceutical compositions are useful in causing gastric hypomotility in a subject and may be used as well in other disorders where gastric motility is beneficially reduced.

The effective daily anti-emptying dose of the compounds will typically be in the range of 0.001 or 0.003 to about 5 mg/day, preferably about 0.001 or 0.05 to 2 mg/day and more preferably about 0.001 or 0.01 to 1 mg/day, for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus. Administration may be by injection, preferably subcutaneous or intramuscular. Orally active compounds may be taken orally, however dosages should be increased 5–10 fold.

Generally, in treating or preventing elevated, inappropriate, or undesired post-prandial blood glucose levels, the compounds of this invention may be administered to patients in need of such treatment in a dosage ranges similar to those given above, however, the compounds are administered more frequently, for example, one, two, or three times a day.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

The following study was carried out to examine the effects of exendin-3 and exendin-4 on gastric emptying and to compare the effects with GLP-1 [7–36]$NH_2$ treatment in rats. This experiment followed a modification of the method of Scarpignato, et al., Arch Int. Pharmacodyn. Ther. 246:286–94 (1980).

Male Harlan Sprague Dawley (HSD) rats were used. All animals were housed at 22.7±0.8 C in a 12:12 hour light:dark cycle (experiments being performed during the light cycle) and were fed and watered ad libitum (Diet LM-485, Teklad, Madison, WIS.). Exendin-3 and exendin-4 were synthesized according to standard peptide synthesis methods.

The determination of gastric emptying by the method described below was performed after a fast of ~20 hours to ensure that the stomach contained no chyme that would interfere with spectrophotometric absorbance measurements.

Conscious rats received by gavage, 1.5 ml of an acaloric gel containing 1.5% methyl cellulose (M-0262, Sigma Chemical Co, St Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In separate experiments on 7 rats, the stomach and small intestine were both excised and opened into an alkaline solution. The quantity of phenol red that could be recovered from the upper gastrointestinal tract within 20 minutes of gavage was 89±4%; dye which appeared to bind irrecoverably to the gut luminal surface may have accounted for the balance. To account for a maximal dye recovery of less than 100%, percent of stomach contents remaining after 20 min were expressed as a fraction of the gastric contents recovered from control rats sacrificed immediately after gavage in the same experiment. Percent gastric contents remaining =(absorbance at 20 min)/(absorbance at 0 mm)×100.

In baseline studies, with no drug treatment, gastric emptying over 20 min was determined. In dose-response studies, rats were treated with 0, 0.01, 0.1, 0.3, 1, 5, 10, or 100 μg of exendin 3, exendin 4, or GLP-1(7–36)NH$_2$. The results are shown in FIG. 2. FIG. 2 shows that exendins 3 and 4 inhibited gastric emptying with approximately the same ED$_{50}$ of 0.1 μg, whereas GLP-1(7–36)NH$_2$ has an ED$_{50}$ of approximately 9 μg, indicating that the exendins are ~90 fold more potent than GLP-1 at inhibiting gastric emptying.

As shown in Table I, exendin-3 and exendin-4 were found to be potent inhibitors of gastric emptying. The effect of rat amylin on gastric emptying is also provided as a second positive control and for comparitive purposes.

TABLE I

| DOSE μg | GLP-1 (7-36) NH$_2$ | | Exendin-3 | | Exendin-4 | | Rat Amylin | |
|---|---|---|---|---|---|---|---|---|
| | % remaining *(n) | SEM | % remaining *(n) | SEM | % remaining *(n) | SEM | % remaining *(n) | SEM |
| Saline Control | 48.00 (16) | 3.50 | 46.760 (15) | 2.360 | 46.000 (17) | 2.000 | 48.00 (17) | 3.5 |
| 0.010 | no data | | 58.240 (3) | 3.180 | no data | 2.000 | 37.60 (2) | 2.50 |
| 0.100 | 42.00 (7) | 6.50 | 70.770 (3) | 5.600 | 72.000 (3) | 12.000 | 52.70 (6) | 6.30 |
| 0.300 | 29.60 (7) | 3.50 | 86.420 (3) | 6.160 | 98.000 (2) | 4.000 | 88.20 (4) | 3.00 |
| 1.000 | 37.20 (9) | 2.70 | 95.330 (3) | 0.790 | 105.000 (1) | 0.000 | 96.80 (9) | 2.80 |
| 3.000 | 56.60 (10) | 6.10 | | | | | 108.00 (4) | 2.70 |
| 10.000 | 87.90 (11) | 2.70 | 101.760 (3) | 3.390 | 112.000 (3) | 2.000 | 101.10 (6) | 3.60 |
| 100.000 | 103.60 (7) | 2.80 | 103.640 (3) | 2.260 | 103.000 (3) | 3.000 | 101.20 (2) | 2.80 |

*percent of gastric contents remaining 20 minutes after gavage.

EXAMPLE 2

Figure 3:
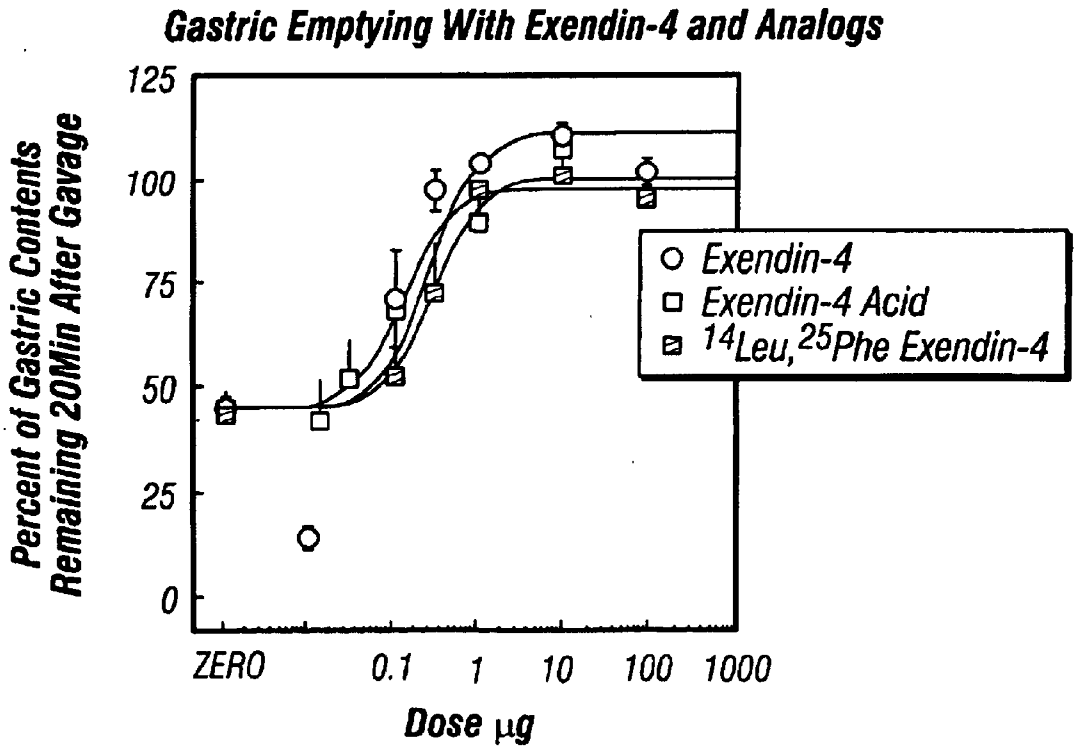
FIG. 3 shows the dose response effects of prior injection of exendin-4 (n=29), exendin-4 acid (n=36) and $^{14}$Leu,$^{25}$Phe exendin-4 (n=36) on the retention of gastric contents 20 minutes after gavage in normal rats. Symbols are means plus or minus standard error of the mean and the curves define the best fitting logistic functions. "Zero" indicates the fraction of gastric contents retained in untreated normal rats.

The effects of exendin-4 analogs on inhibition of gastric emptying were examined, and compared to the effects of exendin-4, according to the methods described in Example 1. Male HSD rats were treated with 0.01, 0.1, 0.3, 1, 10 and 100 μg of exendin-4 0.01, 0.03, 0.1, 1, 10 and 100 μg exendin-4 acid, [SEQ. ID. NO. 36] and 0.1, 0.3, 1, 10 and 100 μg of $^{14}$Leu,$^{25}$Phe exendin-4 [SEQ. ID. NO. 5]. Exendin-3, exendin-4 acid and $^{14}$Leu,$^{25}$Phe were synthesized according to standard peptide synthesis methods. The results, shown in FIG. 3 and Table II, show that the exendin agonists, exendin-4 acid and $^{14}$Leu,$^{25}$Phe exendin-4, are potent inhibitors of gastric emptying. The EC$_{50}$ of exendin-4 was 0.27 μg. The EC$_{50}$ s of exendin-4 acid and $^{14}$Leu,$^{25}$Phe exendin-4 were comparable (0.12 μg and 0.29 μg, respectively).

TABLE II

| Compound | EC$_{50}$ (μg) |
|---|---|
| exendin-4 | 0.27 |
| exendin-4 acid | 0.12 |
| $^{14}$Leu, $^{25}$Phe exendin-4 | 0.29 |

The ability of exendin [9–39], an antagonist of exendin's effects at the cloned GLP-1 receptor, to antagonize the gastric emptying inhibition effect of exendin-4 and GLP-1 [7–36]NH$_2$ was examined according to the methods described in Example 1. Rats were treated with 1.0 μg exendin-4, 1.0 μg exendin-4 with 0.3 mg exendin [9–39], 10 μg GLP-1 [7–36]NH$_2$ 10 μg GLP-1 [7–36]NH$_2$ with 0.3 mg exendin [9–39] or with 0.3 mg exendin 9–39 alone. In these studies, exendin [9–39] was give both subcutaneously (sc) and intravenously (iv). The results of these experiments are shown in FIGS. 4–7.

Figure 4:
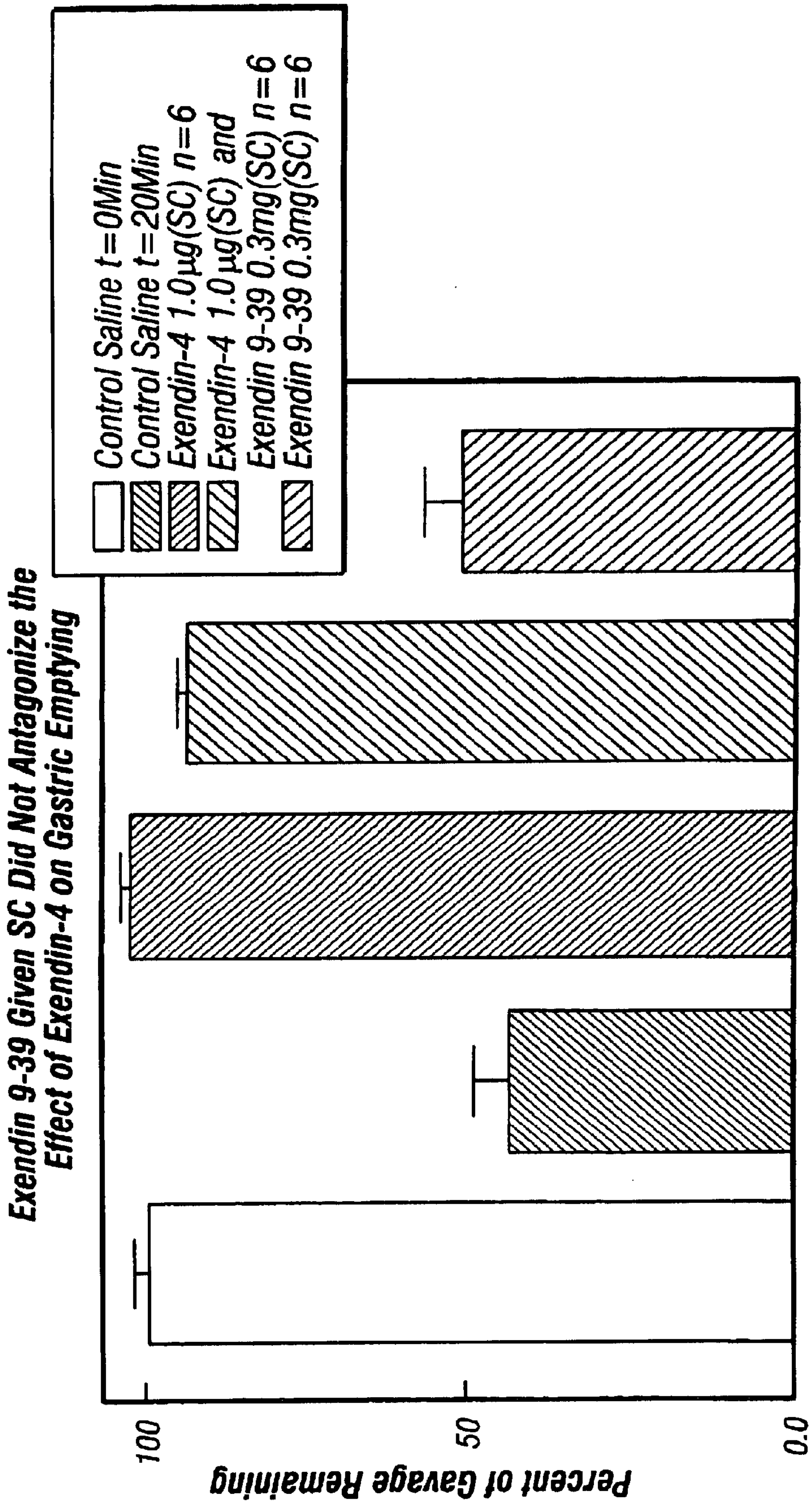
FIG. 4 shows the effect of prior injection of 1.0 μg exendin-4 (sc), n=6; 1.0 μg exendin-4 (sc) plus 0.3 mg exendin [9–39] (sc), n=6; and 0.3 mg exendin [9–39] (sc), n=6 on the retention of gastric contents 20 minutes after gavage. Also shown are saline controls at t=0 and t=20 min. The error bars show standard error of the mean.
Figure 5:
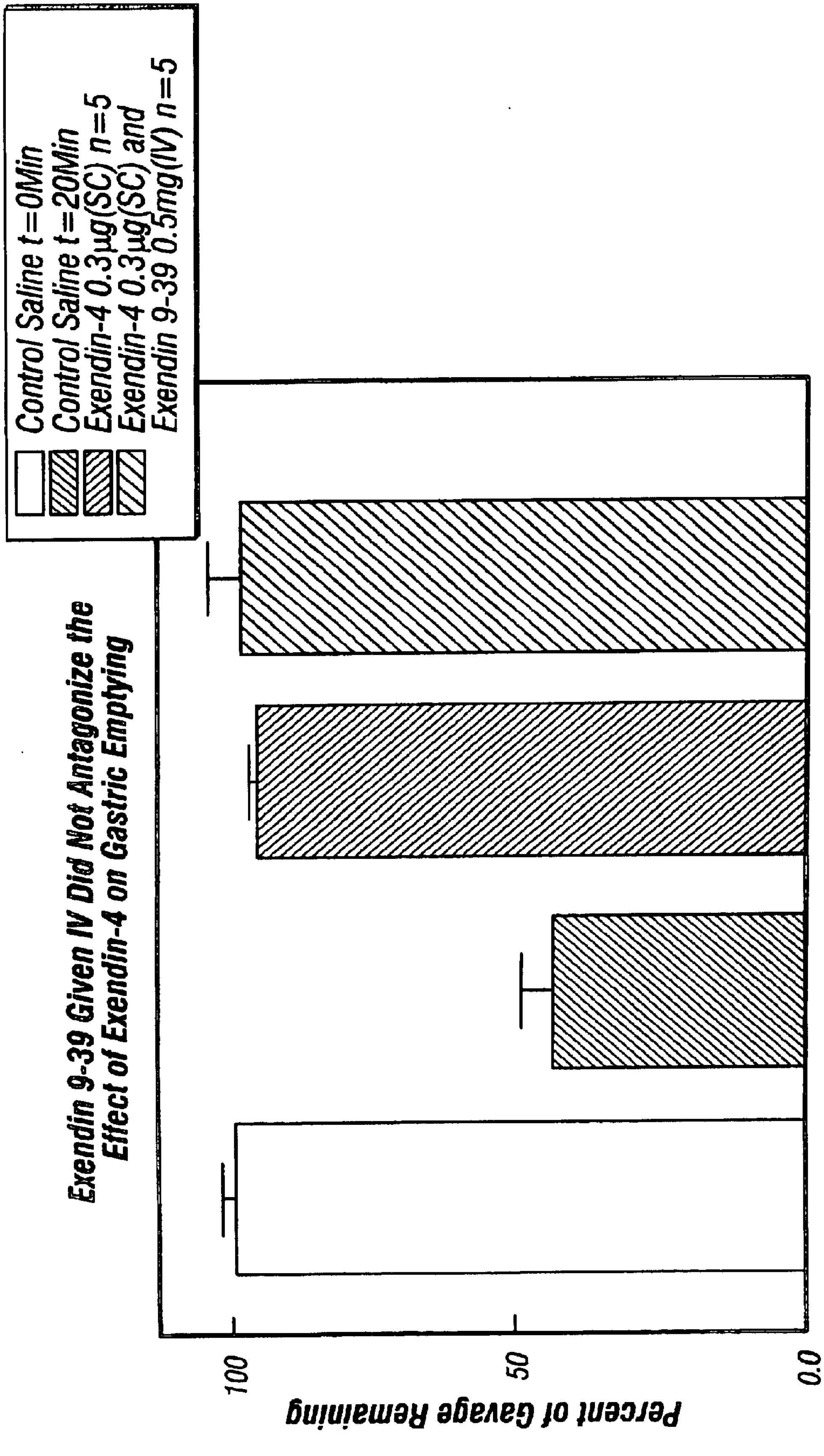
FIG. 5 shows the effect of prior injection of 0.3 μg exendin-4 (sc), n=5 and 0.3 μg exendin-4 (sc) plus 0.5 mg exendin [9–39] (iv), n=5 on the retention of gastric contents 20 minutes after gavage. Also shown are saline controls at t+0 and t=20 min. The error bars show standard error of the mean.
Figure 6:
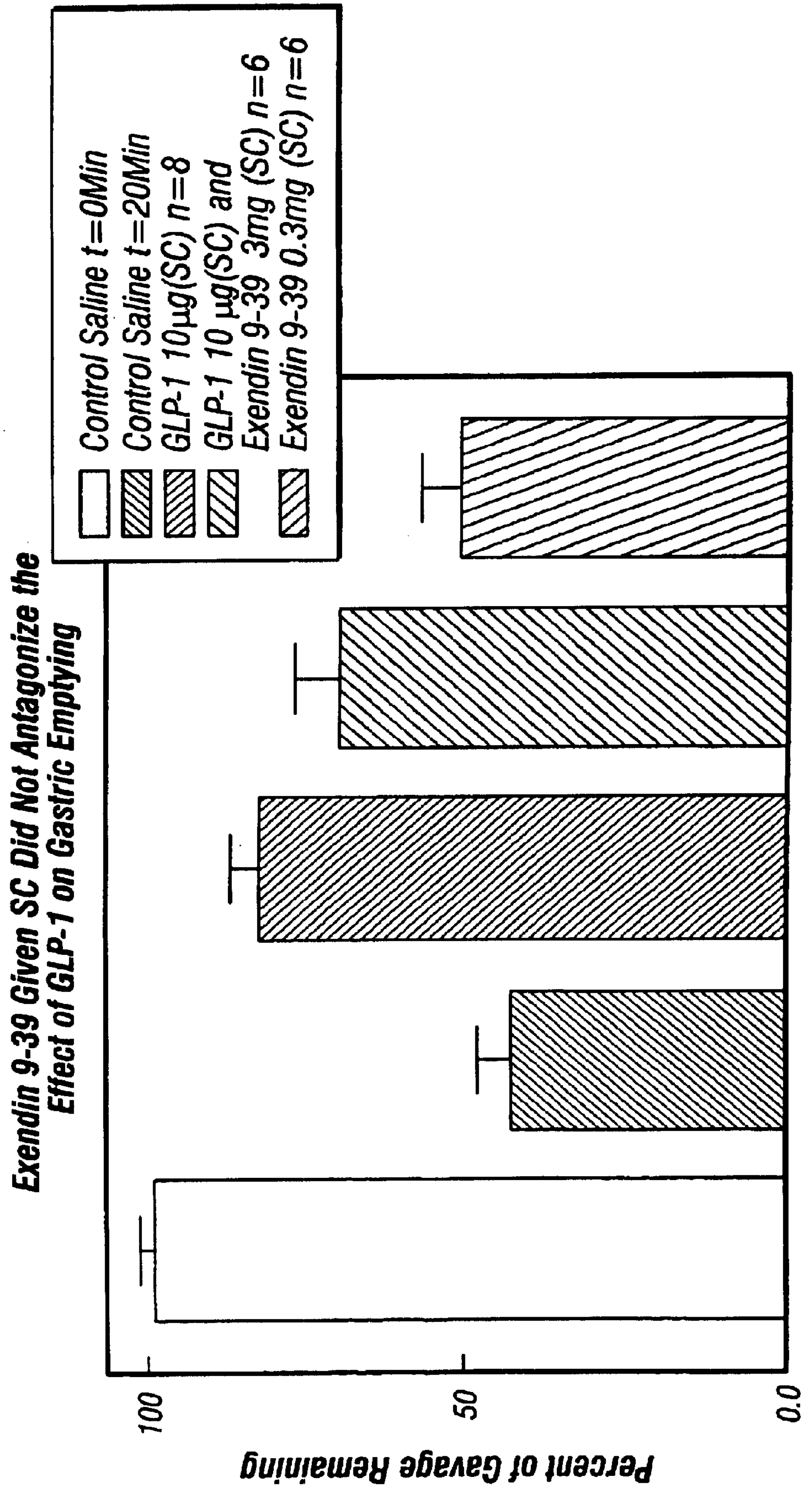
FIG. 6 shows the effect of prior injection of 10 μg GLP-1 [7–36]$NH_2$ (sc), n=8; 10 μg GLP-1 [7–36]$NH_2$ (sc) plus 3 mg exendin [9–39] (sc), n=6; and 0.3 mg exendin [9–39] (sc), n=6 on the retention of gastric contents 20 minutes after gavage. Also shown are saline controls at t=0 and t=20 min. The error bars show standard error of the mean.
Figure 7:
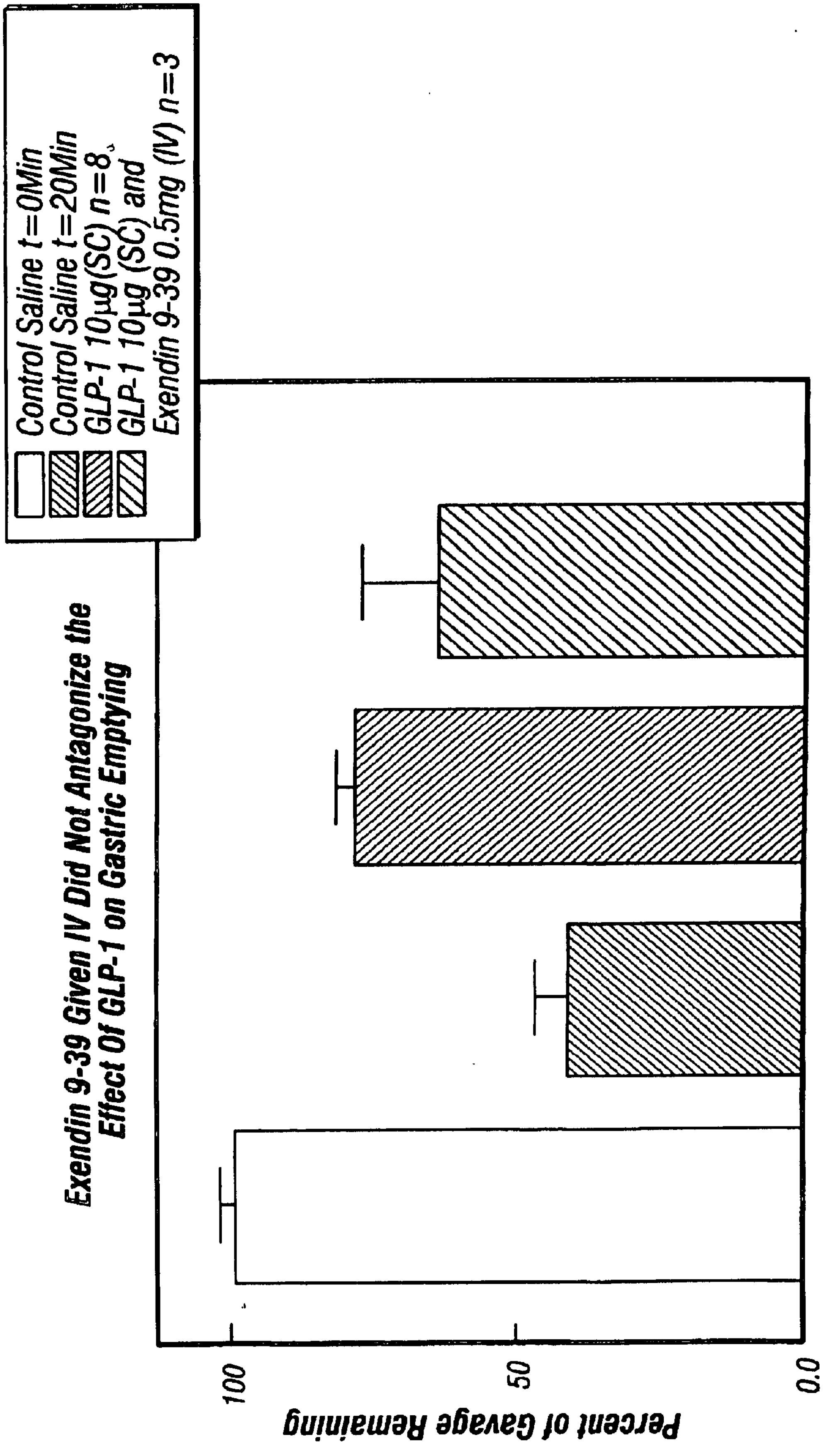
FIG. 7 shows the effect of prior injection of 10 μg GLP-1 [7–36]$NH_2$ (sc), n=8, and 10 μg GLP-1 [7–36]$NH_2$ (sc) plus 0.5 mg exendin [9–39] (iv), n=3 on the retention of gastric contents 20 minutes after gavage. Also shown are saline controls at t=0 and t=20 min. The error bars show standard error of the mean.

As shown in FIGS. 4 and 5, after 20 minutes, the animals treated with exendin-4 showed extremely potent inhibition of gastric emptying, which was not reversed by exendin [9–39]. This occurred regardless of whether the exendin [9–39] was administered sc or iv. Exendin [9–39] alone had no effect on gastric emptying.

As discussed above, exendin [9–39] is a potent antagonist of GLP-1 which binds at the cloned GLP-1 receptor (Fehmann H C, et al., *Peptides* 15(3): 453–6, 1994; Thorens B. et al., *Diabetes* 42(11): 1678–82, 1993). Surprisingly, however, exendin [9–39] did not block the effect of exendin-4 on gastric emptying (see FIGS. 4 and 5). These results indicate that the effects of exendins on gastric emptying are not due binding of the exendins at the cloned GLP-1 receptor, but instead that the gastric emptying effects of exendins are due to a different receptor.

That exendin [9–39] did not block the effect of GLP-1 [7–36]NH$_2$ on gastric emptying (see FIGS. 6 and 7) indicates that, in its effects on gastric emptying, GLP-1 is also acting at a receptor other than the cloned CLP-1 receptor (at which exendin [9–39] is a potent antagonist).

EXAMPLE 4

Preparation of Amidated Peptide Having SEQ. ID. No. [5]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. However, at some positions coupling was less efficient than expected and double couplings were required. In particular, residues Asp$_9$, Thr$_7$ and Phe$_6$ all required double coupling. Deprotection (Fmoc group removal) of the growing peptide chain using piperidine was not always efficient. Double deprotection was required at positions Arg$_{20}$, Val$_{19}$ and Leu$_{14}$. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 55%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 14.5 minutes. Electrospray Mass Spectrometry (M): calculated 4131.7; found 4129.3.

EXAMPLE 5

Preparation of Peptide Having SEQ. ID. NO. [6]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 25% to 75% Solvent B in Solvent A over 30 minutes) of the lyophilized peptide gave product peptide having an observed retention time of 21.5 minutes. Electrospray Mass Spectrometry (M): calculated 4168.6; found 4171.2.

EXAMPLE 6

Preparation of Peptide Having SEQ. ID. NO. [7]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 30% to 60% Solvent B in Solvent A over 30 minutes) of the lyophilized peptide gave product peptide having an observed retention time of 17.9 minutes. Electrospray Mass Spectrometry (M): calculated 4147.6; found 4150.2.

EXAMPLE 7

Preparation of Petide Having SEQ. ID. NO. [8]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 35% to 65% Solvent B in Solvent A over 30 minutes) of the lyophilized peptide gave product peptide having an observed retention time of 19.7 minutes. Electrospray Mass Spectrometry (M): calculated 4212.6; found 4213.2.

EXAMPLE 8

Preparation of Peptide Having SEQ. ID. NO. [9]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 30% to 50% Solvent B in Solvent A over 30 minutes) of the lyophilized peptide gave product peptide having an observed retention time of 16.3 minutes. Electrospray Mass Spectrometry (M): calculated 4262.7; found 4262.4.

EXAMPLE 9

Preparation of Peptide Having SEQ. ID. NO. [10]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6

EXAMPLE 10

Preparation of Peptide Having SEQ. ID. NO. [11]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 11

Preparation of Peptide Having SEQ. ID. NO. [12]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6

EXAMPLE 12

Preparation of Peptide Having SEQ. ID. NO. [13]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4186.6

EXAMPLE 13

Preparation of Peptide Having SEQ. ID. NO. [14]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7

EXAMPLE 14

Preparation of Peptide Having SEQ. ID. NO. [15]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7

EXAMPLE 15

Preparation of Peptide Having SEQ. ID. NO. [16]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4202.7.

EXAMPLE 16

Preparation of Peptide Having SEQ. ID. NO. [17]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 17

Preparation of Peptide Having SEQ. ID. NO. [18]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4184.6.

EXAMPLE 18

Preparation of Peptide Having SEQ. ID. NO. [19]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 19

Preparation of Peptide Having SEQ. ID. NO. [20]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 20

Preparation of Peptide Having SEQ. ID. NO. [21]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 21

Preparation of Peptide Having SEQ. ID. NO. [22]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4115.5.

EXAMPLE 22

Preparation of Peptide Having SEQ. ID. NO. [23]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4188.6.

EXAMPLE 23

Preparation of Peptide Having SEQ. ID. NO. [24]

The above-identified peptide is assembled on 4-(2'-4'-dimethoxyphenyl)-Fmoc aminomethyl phenoxy acetamide norleucine MBRA resin (Novabiochem, 0.55 mmole/g) using Fmoc-protected amino acids (Applied Biosystems, Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4131.6.

EXAMPLE 24

Preparation of Peptide Having SEQ. ID. NO. [25]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 27

Preparation of Peptide Having SEQ. ID. No. [28]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the thioproline positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4246.8.

EXAMPLE 28

Preparation of Peptide Having SEQ. ID. NO. [29]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide.

EXAMPLE 25

Preparation of Peptide Having SEQ. ID. NO. [26]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 26

Preparation of Peptide Having SEQ. ID. NO. [27]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4266.8.

Electrospray Mass Spectrometry (M): calculated 4250.8.

EXAMPLE 29

Preparation of Peptide Having SEQ. ID. NO. [30]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the homoproline positions 38, 37, and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4234.8.

EXAMPLE 30

Preparation of Peptide Having SEQ. ID. NO. [31]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4209.8.

EXAMPLE 31

Preparation of Peptide Having SEQ. ID. NO. [32]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4193.7.

EXAMPLE 32

Preparation of Peptide Having SEQ. ID. NO. [33]

The above-identified peptide is assembled on 4-(2'-4'-dimethoxyphenyl)-Fmoc aminomethyl phenoxy acetamide norleucine MBHA resin (Novabiochem, 0.55 mmole/g). using Fmoc-protected amino acids (Applied Biosystems, Inc.), cleaved from the resin, deprotected and purified in a similar way to Example 1. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3858.2.

EXAMPLE 33

Preparation of Peptide Having SEQ. ID. NO. [34]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the N-methylalanine positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3940.3.

EXAMPLE 34

Preparation of Peptide Having SEQ. ID. NO. [35]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3801.1.

EXAMPLE 35

Preparation of C-terminal Carboxylin Acid Peptides Corresponding to the above C-terminal Amide Sequences The above peptides are assembled on the so called Wang resin (p-alkoxybenzylalacohol resin (Bachem, 0.54 mmole/g)) using Fmoc-protected amino acids (Applied Biosystems, Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

We claim:

1. A method of reducing gastric motility in a subject in need thereof comprising administering to said subject an amount of an exendin effective for reducing gastric motility.

2. A method of delaying gastric emptying in a subject in need thereof comprising administering to said subject an amount of an exendin effective for delaying gastric emptying.

3. The method according to claim 1 or 2 wherein said exendin is exendin-3.

4. The method according to claim 1 or 2 wherein said exendin is exendin-4.

5. The method according to claim 1 or 2 wherein said subject is undergoing a gastrointestinal diagnostic procedure.

6. The method according to claim 5 wherein said gastrointestinal diagnostic procedure is a radiological examination.

7. The method according to claim 6 wherein said gastric gastrointestinal diagnostic procedure is magnetic resonance imaging.

8. The method according to claim 1 or 2 wherein said subject is suffering from a gastrointestinal disorder.

9. A method of reducing gastric motility in a subject in need thereof comprising administering to said subject an amount of an exendin analog effective for reducing gastric motility, wherein said exendin analog is selected from a peptide compound of the formula:

$$\overset{1}{Xaa_1}\ Xaa_2\ Xaa_3\ Gly\ \overset{5}{Thr}\ Xaa_4\ Xaa_5,\ Xaa_6\ Xaa_7\ \overset{10}{Xaa_8}$$

$$Ser\ Lys\ Gln\ Xaa_9\ \overset{15}{Glu}\ Glu\ Glu\ Ala\ Val\ \overset{20}{Arg}\ Leu$$

$$Xaa_{10}\ Xaa_{11}\ Xaa_{12}\ \overset{25}{Xaa_{13}}\ Leu\ Lys\ Asn\ Gly\ \overset{30}{Gly}\ Xaa_{14}$$

$$Ser\ Ser\ Gly\ \overset{35}{Ala}\ Xaa_{15}\ Xaa_{16}\ Xaa_{17}\ Xaa_{18}\text{-}Z$$

wherein:

$Xaa_1$ is His, Arg or Tyr;

$Xaa_2$ is Ser, Gly, Ala or Thr;

$Xaa_3$ is Asp or Glu;

$Xaa_4$ is Phe, Tyr or naphthylalanine;

$Xaa_5$ is Thr or Ser;

$Xaa_6$ is Ser or Thr;

$Xaa_7$ is Asp or Glu;

$Xaa_8$ is Leu, Ile, Val, pentylglycine or Met;

$Xaa_9$ is Leu, Ile, pentylglycine, Val or Met;

$Xaa_{10}$ is Phe, Tyr or naphthylalanine;

$Xaa_{11}$ is Ile, Val, Leu, pentylglycine, tert-butylglycine or Met;

$Xaa_{12}$ is Glu or Asp;

$Xaa_{13}$ is Trp, Phe, Tyr, or naphthylalanine;

$Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine;

$Xaa_{18}$ is Ser, Thr or Tyr; and

Z is —OH or —$NH_2$;

with the proviso that the compound does not have the formula of either exendin-3 or exendin-4 and pharmaceutically acceptable salts thereof.

10. A method of reducing gastric motility in a subject in need thereof comprising administering to said subject an amount of an exendin analog effective for reducing gastric motility, wherein said exendin analog is selected from a peptide compound of the formula:

```
1                  5                      10
Xaa1 Xaa2 Xaa3 Gly Thr Xaa4 Xaa5, Xaa6 Xaa7 Xaa8

                   15                  20
Ser Lys Gln Xaa9 Glu Glu Glu Ala Val Arg Leu

                   25                      30
Xaa10 Xaa11 Xaa12 Xaa13 Leu Lys Asn Gly Gly Xaa14

              35
Ser Ser Gly Ala Xaa15 Xaa16 Xaa17 Xaa18-Z
```

wherein:

$Xaa_1$ is His or Arg;

$Xaa_2$ is Ser or Gly;

$Xaa_3$ is Asp or Glu;

$Xaa_4$ is Phe or naphthylalanine;

$Xaa_5$ is Thr or Ser;

$Xaa_6$ is Ser or Thr;

$Xaa_7$ is Asp or Glu;

$Xaa_8$ is Leu or pentylglycine $Xaa_9$ is Leu or pentylglycine;

$Xaa_{10}$ is Phe or naphthylalanine;

$Xaa_{11}$ is Ile, Val or tert-butylglycine;

$Xaa_{12}$ is Glu or Asp;

$Xaa_{13}$ is Trp or Phe;

$Xaa_{14}$, $Xaa_{15}$, $Xaa_{16}$ and $Xaa_{17}$ are independently selected from Pro, homoproline or N-methylalanine;

$Xaa_{18}$ is Ser or Tyr; and

Z is —OH or —$NH_2$;

with the proviso that the compound does not have the formula of either exendin-3 or exendin-4 and pharmaceutically acceptable salts thereof.

11. A method of delaying gastric emptying in a subject in need thereof comprising administering to said subject an amount of an exendin analog effective for delaying gastric emptying, wherein said exendin analog is selected from a peptide compound of the formula:

```
1                  5                      10
Xaa1 Xaa2 Xaa3 Gly Thr Xaa4 Xaa5, Xaa6 Xaa7 Xaa8

                   15                  20
Ser Lys Gln Xaa9 Glu Glu Glu Ala Val Arg Leu

                   25                      30
Xaa10 Xaa11 Xaa12 Xaa13 Leu Lys Asn Gly Gly Xaa14

              35
Ser Ser Gly Ala Xaa15 Xaa16 Xaa17 Xaa18-Z
```

wherein:

$Xaa_1$ is His, Arg or Tyr;

$Xaa_2$ is Ser, Gly, Ala or Thr;

$Xaa_3$ is Asp or Glu;

$Xaa_4$ is Phe, Tyr or naphthylalanine;

$Xaa_5$ is Thr or Ser;

$Xaa_6$ is Ser or Thr;

$Xaa_7$ is Asp or Glu;

$Xaa_8$ is Leu, Ile, Val, pentylglycine or Met;

$Xaa_9$ is Leu, Ile, pentylglycine, Val or Met;

$Xaa_{10}$ is Phe, Tyr or naphthylalanine;

$Xaa_{11}$ is Ile, Val, Leu, pentylglycine, tert-butylglycine or Met;

$Xaa_{12}$ is Glu or Asp;

$Xaa_{13}$ is Trp, Phe, Tyr, or naphthylalanine;

$Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine;

$Xaa_{18}$ is Ser, Thr or Tyr; and

Z is —OH or —$NH_2$;

with the proviso that the compound does not have the formula of either exendin-3 or exendin-4 and pharmaceutically acceptable salts thereof.

12. A method of delaying gastric emptying in a subject in need thereof comprising administering to said subject an amount of an exendin analog effective for delaying gastric emptying, wherein said exendin analog is selected from a peptide compound of the formula:

```
1                  5                      10
Xaa1 Xaa2 Xaa3 Gly Thr Xaa4 Xaa5, Xaa6 Xaa7 Xaa8

                   15                  20
Ser Lys Gln Xaa9 Glu Glu Glu Ala Val Arg Leu

                   25                      30
Xaa10 Xaa11 Xaa12 Xaa13 Leu Lys Asn Gly Gly Xaa14

              35
Ser Ser Gly Ala Xaa15 Xaa16 Xaa17 Xaa18-Z
```

wherein:

$Xaa_1$ is His or Arg;

$Xaa_2$ is Ser or Gly;

$Xaa_3$ is Asp or Glu;

$Xaa_4$ is Phe or naphthylalanine;

$Xaa_5$ is Thr or Ser;

$Xaa_6$ is Ser or Thr;

$Xaa_7$ is Asp or Glu;

$Xaa_8$ is Leu or pentylglycine $Xaa_9$ is Leu or pentylglycine;

$Xaa_{10}$ is Phe or naphthylalanine;

$Xaa_{11}$ is Ile, Val or tert-butylglycine;

$Xaa_{12}$ is Glu or Asp;

$Xaa_{13}$ is Trp or Phe;

$Xaa_{14}$, $Xaa_{15}$, $Xaa_{16}$ and $Xaa_{17}$ are independently selected from Pro, homoproline or N-methylalanine;

$Xaa_{18}$ is Ser or Tyr; and

Z is —OH or —$NH_2$;

with the proviso that the compound does not have the formula of either exendin-3 or exendin-4 and pharmaceutically acceptable salts thereof.

13. The method according to claim 9, 10, 11, or 12 wherein said subject is undergoing a gastrointestinal diagnostic procedure.

14. The method according to claim 13 wherein said gastrointestinal diagnostic procedure is a radiological examination.

15. The method according to claim 14 wherein said gastric gastrointestinal diagnostic procedure is magnetic resonance imaging.

16. The method according to claim 9, 10, 11, or 12 wherein said subject is suffering from a gastrointestinal disorder.

17. A method of reducing gastric motility in a subject in need thereof comprising administering to said subject an amount of exendin-4 effective for reducing gastric motility.

18. A method of delaying gastric emptying in a subject in need thereof comprising administering to said subject an amount of exendin-4 effective for delaying gastric emptying.

19. The method according to claim 17 or 18 wherein said subject is undergoing a gastrointestinal diagnostic procedure.

20. The method according to claim 19 wherein said gastrointestinal diagnostic procedure is a radiological examination.

21. The method according to claim 20 wherein said gastric gastrointestinal diagnostic procedure is magnetic resonance imaging.

22. The method according to claim 17 or 18 wherein said subject is suffering from a gastrointestinal disorder.

* * * * *

UNITED STATES PATENT AND TRADEMARK OFFICE

CERTIFICATE OF CORRECTION

PATENT NO. : 6,858,576 B1
DATED : February 22, 2005
INVENTOR(S) : Andrew A. Young et al.

It is certified that error appears in the above-identified patent and that said Letters Patent is hereby corrected as shown below:

Title page,
Item [*] Notice, replace with the following text:
-- Notice: Subject to any disclaimer, the term of this patent is extended or adjusted under 35 U.S.C. 154(b) by 151 days. --.

Signed and Sealed this

Thirtieth Day of August, 2005

JON W. DUDAS
*Director of the United States Patent and Trademark Office*